United States Patent
Adachi

(10) Patent No.: US 12,123,826 B2
(45) Date of Patent: Oct. 22, 2024

(54) IMAGE PROCESSING DEVICE, IMAGING SYSTEM, IMAGE PROCESSING METHOD, AND COMPUTER-READABLE RECORDING MEDIUM

(71) Applicant: OLYMPUS CORPORATION, Hachioji (JP)

(72) Inventor: Satoru Adachi, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 72 days.

(21) Appl. No.: 17/879,867

(22) Filed: Aug. 3, 2022

(65) Prior Publication Data

US 2022/0377202 A1 Nov. 24, 2022

Related U.S. Application Data

(63) Continuation of application No. PCT/JP2020/005182, filed on Feb. 10, 2020.

(51) Int. Cl.
| | |
|---|---|
| *G01N 21/31* | (2006.01) |
| *H04N 1/21* | (2006.01) |
| *H04N 23/50* | (2023.01) |
| *H04N 23/611* | (2023.01) |
| *H04N 23/617* | (2023.01) |
| *H04N 23/68* | (2023.01) |

(52) U.S. Cl.
CPC ........... *G01N 21/31* (2013.01); *H04N 1/2145* (2013.01); *H04N 23/611* (2023.01); *H04N 23/617* (2023.01); *H04N 23/684* (2023.01); *H04N 23/555* (2023.01)

(58) Field of Classification Search
CPC .... G01N 21/31; H04N 1/2145; H04N 23/611; H04N 23/617; H04N 23/684; H04N 23/555; G02B 21/365; G02B 23/2484; A61B 1/267

USPC .................................................. 348/208.12
See application file for complete search history.

(56) References Cited

U.S. PATENT DOCUMENTS

| | | | |
|---|---|---|---|
| 2008/0232766 A1 | 9/2008 | Van Quickelberge | |
| 2009/0102938 A1* | 4/2009 | Takahashi | H04N 23/63 348/222.1 |
| 2012/0105664 A1* | 5/2012 | Kang | G06V 20/41 348/222.1 |

FOREIGN PATENT DOCUMENTS

| | | |
|---|---|---|
| JP | 2002-219104 A | 8/2002 |
| JP | 2004-97442 A | 4/2004 |
| JP | 2009-506694 A | 2/2009 |

(Continued)

OTHER PUBLICATIONS

International Search Report dated Apr. 14, 2020, issued in counterpart International Application No. PCT/JP2020/005182 (3 pages).

*Primary Examiner* — Lin Ye
*Assistant Examiner* — Chan T Nguyen
(74) *Attorney, Agent, or Firm* — WHDA, LLP

(57) ABSTRACT

An image processing device includes: a processor including hardware. The processor is configured to: obtain images captured by an imaging element configured to perform imaging at a higher frequency than a vibrational frequency of a subject; detect the vibrational frequency of the subject based on the obtained images; set a selection period that is longer than a vibration period of the subject; sequentially select, from among the obtained images, images to be displayed on a display based on the selection period; and output the selected images.

10 Claims, 15 Drawing Sheets

(56) References Cited

FOREIGN PATENT DOCUMENTS

| | | |
|---|---|---|
| JP | 2009-100326 A | 5/2009 |
| JP | 2012-99979 A | 5/2012 |
| JP | 2016-52453 A | 4/2016 |
| WO | 2017/150836 A1 | 9/2017 |

* cited by examiner

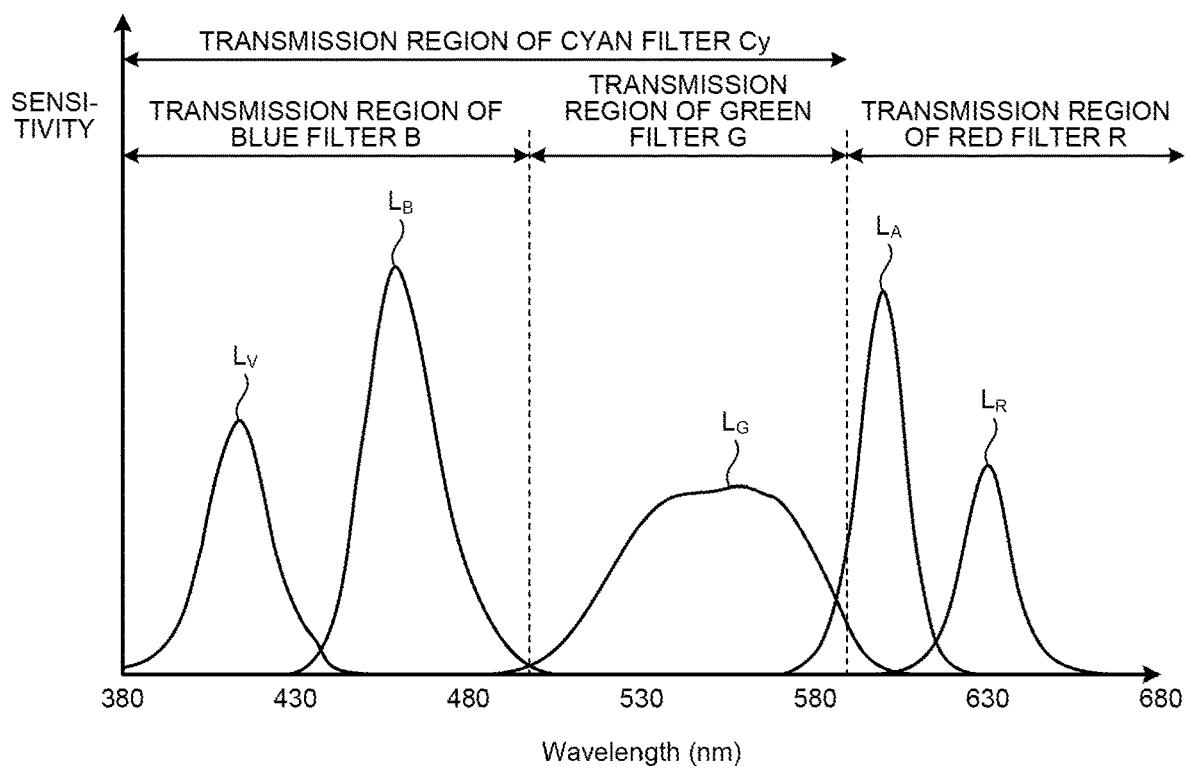

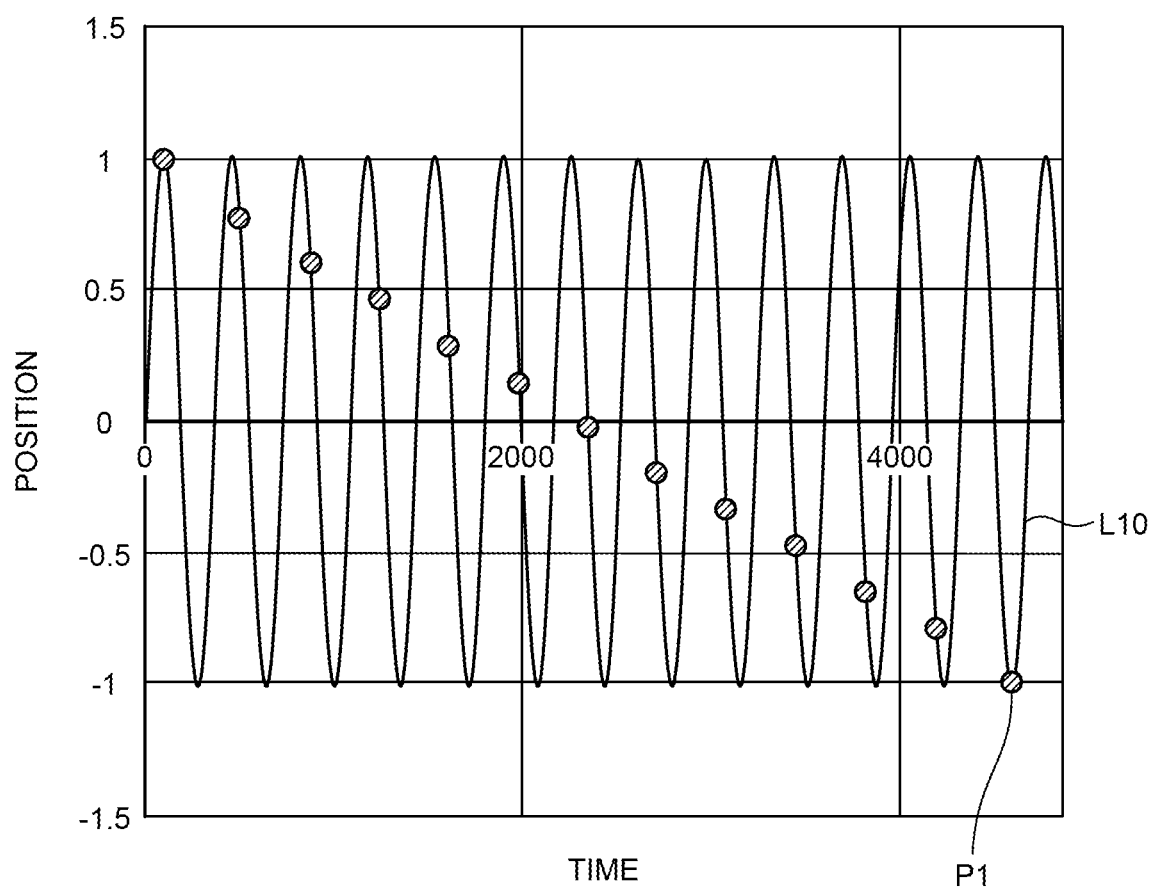

IMAGE PROCESSING DEVICE, IMAGING SYSTEM, IMAGE PROCESSING METHOD, AND COMPUTER-READABLE RECORDING MEDIUM

CROSS-REFERENCE TO RELATED APPLICATION

This application is a continuation of International Application No. PCT/JP2020/005182, filed on Feb. 10, 2020, the entire contents of which are incorporated herein by reference.

BACKGROUND

1. Technical Field

The present disclosure is related to an image processing device that enables observation, in real time, of the actions of a photographic subject performing high-speed vibration, high-speed rotation, or high-speed movement as captured by an imaging device, and that selects display images to be displayed in a display monitor from an image group generated as a result of capturing the actions of the photographic subject. Moreover, the disclosure is related to an imaging system, an image processing method, and a computer-readable recording medium.

2. Related Art

A technology is known that, in an imaging system, enables normal observation in which a continuous light is emitted, and enables stroboscopic observation in which a stroboscopic light is emitted at predetermined timings (for example, Japanese Patent Application Laid-open No. 2004-97442). In regard to that technology, a microphone is installed for detecting the vibrational frequency of vocal cords, and images are captured at the timings at which a pulsed stroboscopic light is emitted in synchronization with the vibrational frequency of the vocal cords as detected by the microphone. After the images are sequentially recorded, a plurality of images is reproduced in chronological order. That enables observation of the vocal cords of a subject, which undergo high-speed vibration, while stopping the playback or in slow-motion playback.

SUMMARY

In some embodiments, an image processing device includes: a processor comprising hardware, the processor being configured to: obtain images captured by an imaging element configured to perform imaging at a higher frequency than a vibrational frequency of a subject; detect the vibrational frequency of the subject based on the obtained images; set a selection period that is longer than a vibration period of the subject; sequentially select, from among the obtained images, images to be displayed on a display based on the selection period; and output the selected images.

In some embodiments, an imaging system includes: the image processing device; and an imaging device. The imaging device includes an imaging element configured to perform imaging at a higher frequency than a vibrational frequency of the subject.

In some embodiments, provided is an image processing method implemented in an image processing device. The method includes: obtaining images captured by an imaging element configured to perform imaging at a higher frequency than a vibrational frequency of a subject; detecting the vibrational frequency of the subject based on the obtained images; setting a selection period that is longer than a vibration period of the subject; sequentially selecting, from among the obtained images, images to be displayed on a display based on the selection period; and outputting the selected images.

In some embodiments, provided is a non-transitory computer-readable recording medium with an executable program stored thereon. The program causes an image processing device to perform: obtaining images captured by an imaging element configured to perform imaging at a higher frequency than a vibrational frequency of a subject; detecting the vibrational frequency of the subject based on the obtained images; setting a selection period that is longer than a vibration period of the subject; sequentially selecting, from among the obtained images, images to be displayed on a display based on the selection period; and outputting the selected images.

The above and other features, advantages and technical and industrial significance of this disclosure will be better understood by reading the following detailed description of presently preferred embodiments of the disclosure, when considered in connection with the accompanying drawings.

BRIEF DESCRIPTION OF THE DRAWINGS

FIG. 4 is a diagram that schematically illustrates a layout of a color filter;

FIG. 5 is a diagram that schematically illustrates the sensitivity and the wavelength bandwidth of each filter;

FIG. 6 is a diagram that schematically illustrates the overview of the conventional observation method for observing a subject;

FIG. 9 is a diagram that schematically illustrates the vibrational frequency of the vocal cords of a subject;

DETAILED DESCRIPTION

Figure 1:
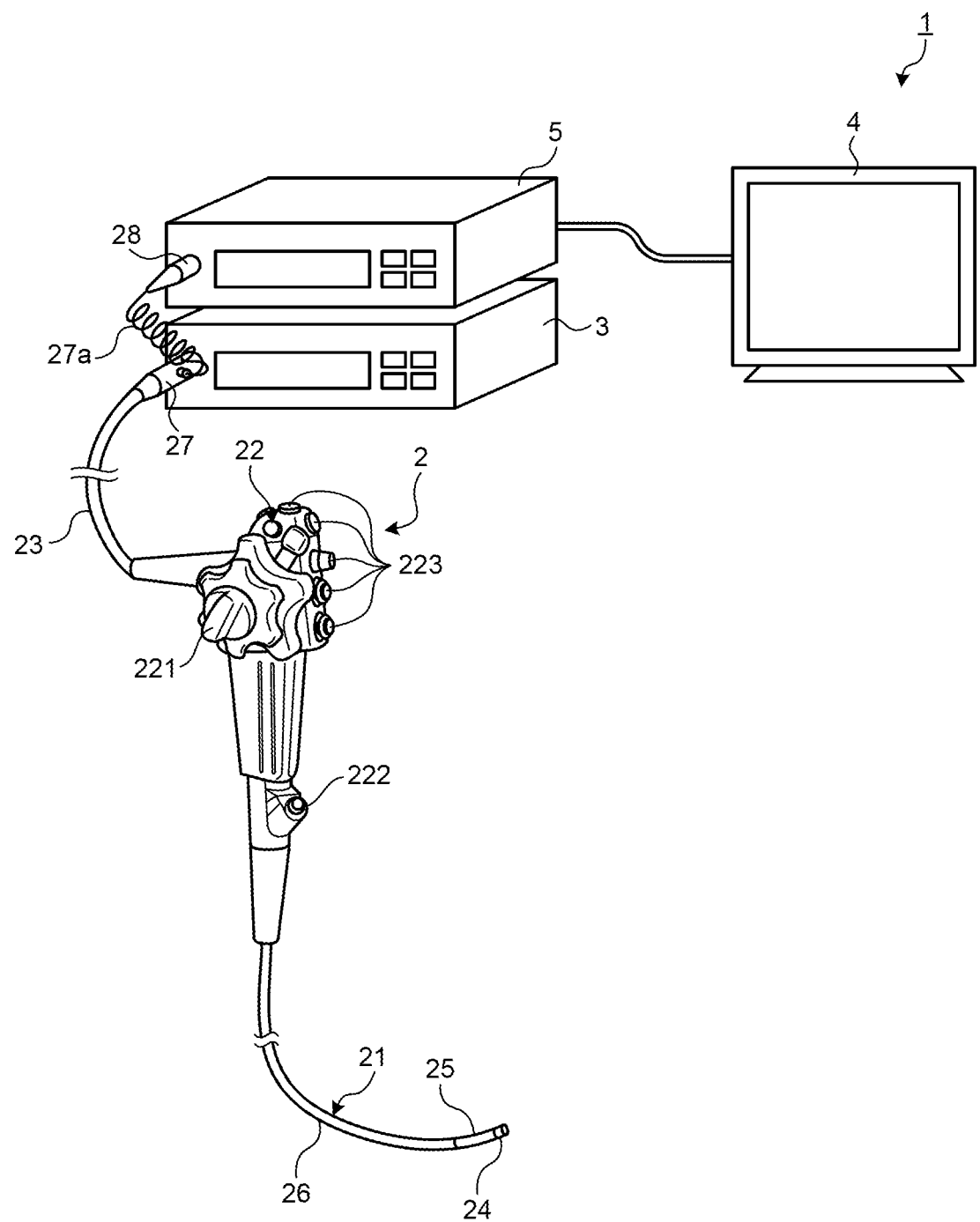
FIG. 1 is an overall configuration diagram of an imaging system according to a first embodiment.

Regarding the scope of the disclosure, it is possible to think of a variety of targets, such as vocal cords undergoing high-speed vibration, a motor performing high-speed rotation, and an object performing a high-speed movement. Herein, as an example, the explanation is given about observing, in real time, the vibrations of vocal cords that undergo high-speed vibration. Exemplary embodiments of the disclosure are described below in detail with reference to the drawings. However, the disclosure is not limited by the embodiments described below. Moreover, in the following explanation given with reference to the drawings; the shapes, the sizes, and the positional relationships are schematically illustrated only to the extent of enabling understanding of the details of the disclosure. That is, the disclosure is not limited to the shapes, the sizes, and the positional relationships illustrated in the drawings.

First Embodiment

Configuration of Imaging System

Figure 2:
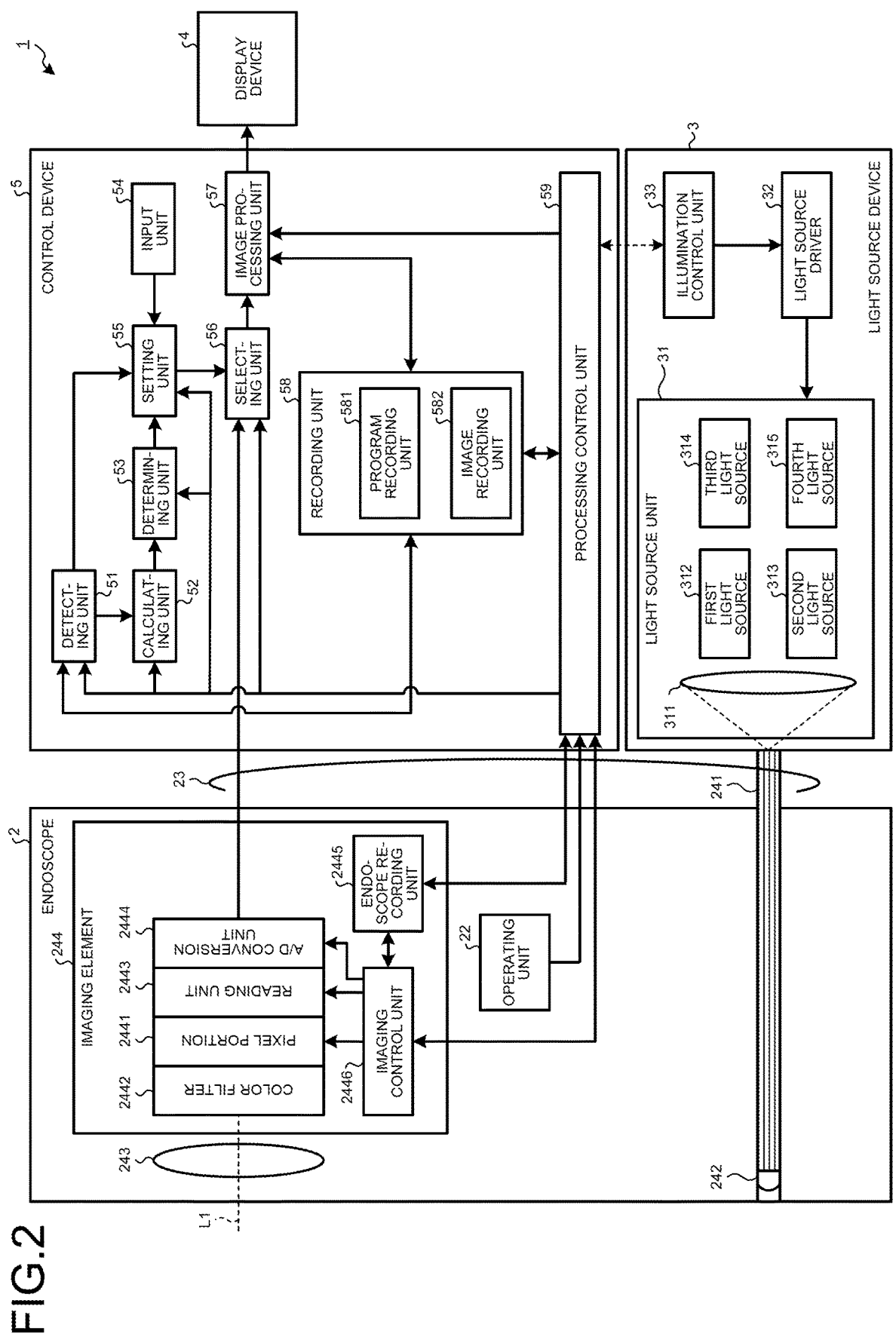
FIG. 2 is a block diagram illustrating a functional configuration of the main parts of the imaging system according to the first embodiment.

FIG. 1 is an overall configuration diagram of an imaging system according to a first embodiment. FIG. 2 is a block diagram illustrating a functional configuration of the main parts of the imaging system according to the first embodiment. The constituent elements are meant for observing, in real time, the vibrations of vocal cords that undergo high-speed vibration. The vocal cords undergoing high-speed vibration represent an example of the scope of the disclosure that includes a variety of possible targets.

An imaging system 1 illustrated in FIGS. 1 and 2 takes images of the inside of the body of a subject such as a patient or images of the vocal cords of the subject after an endoscope is inserted inside the subject, the subject representing a photographic subject; and displays, in a display device, display images based on the image data obtained as a result of performing imaging. Then, the user such as a doctor observes the display images displayed in the display device, and inspects for the presence or absence of abnormal regions such as bleeding sites, tumor sites, or abnormal sites representing a target inspection sites; and examines the condition of the vocal cords. The imaging system 1 includes an endoscope 2, a light source device 3, a display device 4, and a control device 5.

Configuration of Endoscope

Firstly, the explanation is given about a configuration of the endoscope 2.

The endoscope 2 generates images based on image data (RAW data) obtained as a result of performing imaging of the inside of the body of the subject or performing imaging of the vocal cords of the subject, and outputs the generated image data to the control device 5. The endoscope 2 includes an insertion portion 21, an operating unit 22, and a universal cord 23.

The insertion portion 21 is flexible in nature and is elongated in shape. The insertion portion 21 includes the following: a front end portion 24 which has an imaging element 244 (explained later) built-in; a freely-bendable curved portion 25 that is made of a plurality of bent pieces; and a flexible tube 26 that is a flexible and elongated tube connected to the proximal end of the curved portion 25.

The front end portion 24 is made of fiberglass, and includes the following: a light guide 241 constituting a light guiding path for the light supplied from the light source device 3; an illumination lens 242 that is disposed at the front end of the light guide 241; an optical system 243 that collects light; and the imaging element 244 that is disposed at the image formation position of the optical system 243.

The imaging element 244 includes a plurality of pixels arranged in a two-dimensional manner. Each pixel performs photoelectric conversion and generates an electrical signal corresponding to the light reception amount of the light collected by the optical system 243. The imaging element 244 is configured using an image sensor such as a complementary metal oxide semiconductor (CMOS). More particularly, the imaging element 244 includes a two-dimensional arrangement of a plurality of pixels that receives light, performs photoelectric conversion of the light, and outputs electrical signals. The imaging element 244 performs imaging of the inside of the body of the subject or performs imaging of the vocal cords of the subject at a predetermined imaging frame rate, and outputs image data (RAW data). The imaging element 244 includes a pixel portion 2441, a color filter 2442, a reading unit 2443, an A/D conversion unit 2444, an endoscope recording unit 2445, and an imaging control unit 2446.

The pixel portion 2441 includes a plurality of pixels arranged as a two-dimensional matrix. The pixels perform photoelectric conversion and generate electrical signals corresponding to the light reception amount, and output the electrical signals.

Circuit Configuration of Pixel Portion

Figure 3:
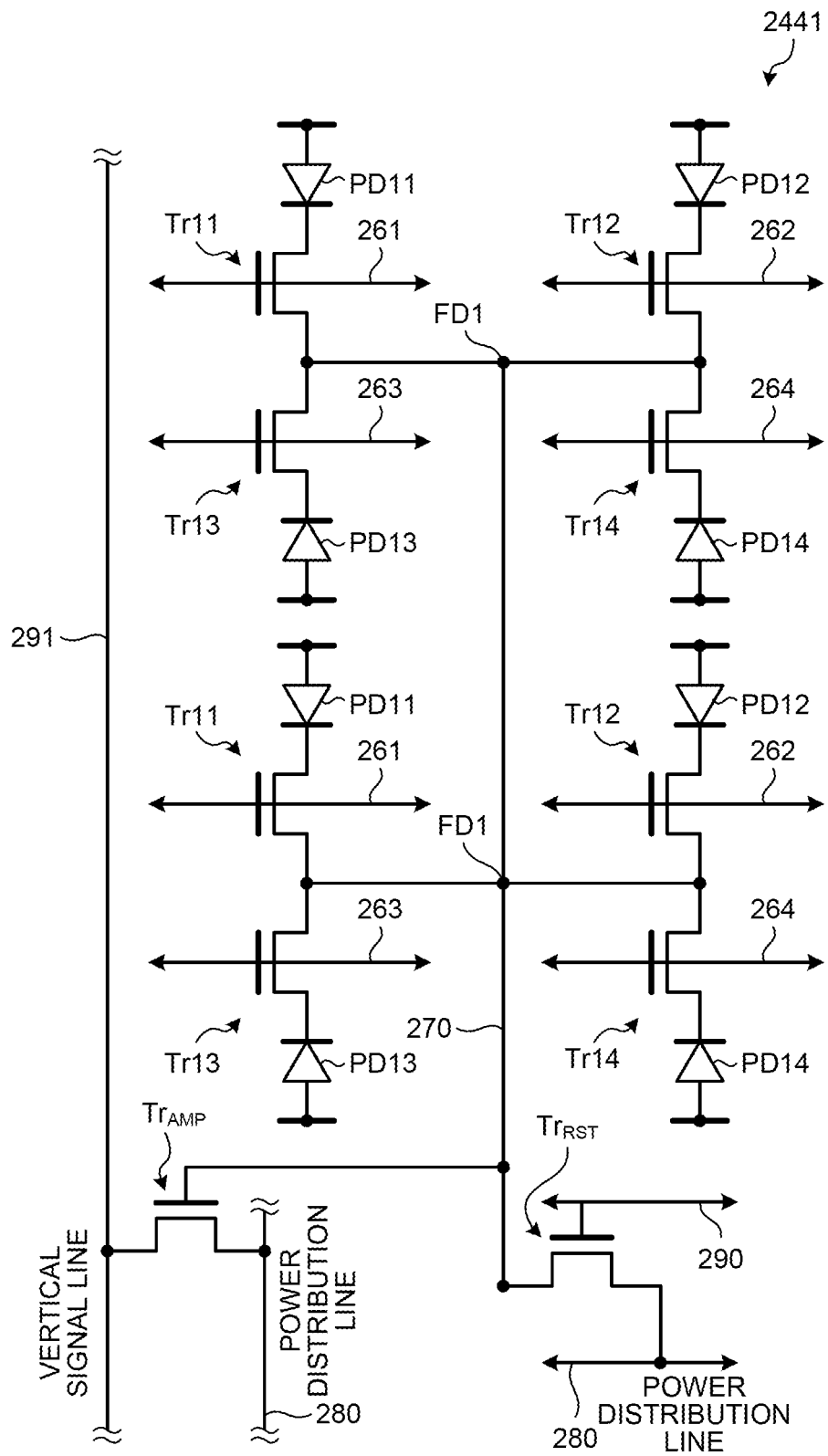
FIG. 3 is a diagram illustrating some part of a circuit configuration of a pixel portion.

Given below is the detailed explanation of a circuit configuration of the pixel portion 2441. FIG. 3 is a diagram illustrating some part of the circuit configuration of the pixel portion 2441. In FIG. 3, in order to simplify the explanation, a set of four pixels (2×2) represent the smallest pixel unit in the pixel portion 2441.

As illustrated in FIG. 3, the pixel portion 2441 outputs electrical signals via a charge-voltage conversion unit FD1 made of four pixels (2×2). The pixel portion 2441 includes four photoelectric devices PD (PD11, PD12, PD13, and PD14); the charge-voltage conversion unit FD1; four transfer transistors Tr (Tr11, Tr12, Tr13, and Tr14); a charge-voltage conversion reset transistor $Tr_{RST}$; and a pixel output transistor $Tr_{AMP}$. In the first embodiment, the four photoelectric devices PD (PD11, PD12, PD13, and PD14) and the four transfer transistors Tr (Tr11, Tr12, Tr13, and Tr14), which are meant for transferring the signal charge from the photoelectric conversion devices PD to the charge-voltage conversion unit FD1, are called unit pixels (2×2 unit pixels).

The photoelectric conversion devices PD1/ to PD14 perform photoelectric conversion of the incident light into a signal charge quantity corresponding to the amount of the incident light, and accumulate the signal charge quantity. Regarding the photoelectric conversion devices PD11 to PD14, the cathode sides are connected to the source side of the transfer transistors Tr11 to Tr14, respectively; and the anode sides are connected to ground GND.

The transfer transistors Tr11 to Tr14 transfer the electrical charge from the photoelectric conversion devices PD11 to PD14, respectively, to the charge-voltage conversion unit FD1. The drain of each of the transfer transistors Tr11 to Tr14 is connected to the source of the charge-voltage conversion reset transistor $Tr_{RST}$. Moreover, the gates of the transfer transistors Tr11 to Tr14 are connected to signal lines 261 to 264, respectively, to which independent row-reading driving pulses are applied.

The charge-voltage conversion unit FD1 is made of a floating diffusion and converts the electrical charge, which is accumulated in the photoelectric conversion devices PD11 to PD14, into a voltage. The charge-voltage conversion unit FD1 is connected to the gate of the pixel output transistor $Tr_{AMP}$ via a signal line 270.

Of the charge-voltage conversion reset transistor $Tr_{RST}$, the drain is connected to a power distribution line 280; and the gate has a reset wiring 290, to which a reset pulse is applied, connected thereto. The charge-voltage conversion reset transistor $Tr_{RST}$ resets the charge-voltage conversion unit FD1 to a predetermined electrical potential.

Of the pixel output transistor $Tr_{AMP}$, the source is connected to a vertical signal line 291, and the drain is connected to the power distribution line 280. The pixel output transistor $Tr_{AMP}$ outputs, to the vertical signal line 291, electric signals that are voltage-converted by the charge-voltage conversion unit FD1. When the charge-voltage conversion unit FD1 is reset to a predetermined voltage by the charge-voltage conversion reset transistor $Tr_{RST}$, the pixel output transistor $Tr_{AMP}$ switches to the on state and outputs, to the vertical signal line 291, electric signals that are voltage-converted by the charge-voltage conversion unit FD1.

Under the control of the imaging control unit 2446, the pixel portion 2441 configured in the manner explained above transfers the electrical charge, which is accumulated in the photoelectric conversion devices PD1*l* to PD14, via the transfer transistors Tr11 to Tr14. Then, the electrical signals that are voltage-converted by the charge-voltage conversion unit FD1 are input to the gate of the pixel output transistor $Tr_{AMP}$ via the signal line 270. As a result, the electrical signals get amplified and are output to the vertical signal line 291. Subsequently, the charge-voltage conversion unit FD1 is reset to a predetermined electrical potential by the charge-voltage conversion reset transistor $Tr_{RST}$, and the pixel output transistor $Tr_{AMP}$ switches to the off state.

Configuration of Color Filter

Given below is the explanation of a configuration of the color filter 2442. FIG. 4 is a diagram that schematically illustrates a layout of the color filter 2442.

As illustrated in FIG. 4, a unit pixel (2×2) is configured as a single filter unit, and each filer is placed on the light receiving surface of each of the photoelectric conversion devices PD11 to PD14. Each filter unit U1 is configured using at least either a blue filer or a red filter R; a green filter G; and two or more special filters. The blue filter B transmits the light having the wavelength bandwidth of the blue color. The red filter R transmits the light having the wavelength bandwidth of the red color. The green filter G transmits the light having the wavelength bandwidth of the green color. The special filters are configured using cyan filters Cy. The cyan filters Cy transmit at least two or more lights including the light having the wavelength bandwidth of the blue color and the light having the wavelength bandwidth of the green color.

FIG. 5 is a diagram that schematically illustrates the sensitivity and the wavelength bandwidth of each filter. In FIG. 5, the horizontal axis represents the wavelength (nm), and the vertical axis represents the sensitivity. Moreover, in FIG. 5, a curved line $L_V$ indicates the sensitivity of the violet color, a curved line $L_B$ indicates the sensitivity of the blue color, a curved line $L_G$ indicates the sensitivity of the green color, a curved line $L_A$ indicates the sensitivity of the umber color, and a curved line $L_R$ indicates the sensitivity of the red color.

As illustrated in FIG. 5, the cyan filter Cy transmits the light having the wavelength bandwidth of the blue color and the light having the wavelength bandwidth of the green color. In the following explanation, a photoelectric conversion device PD configured by arranging the red filter R on the light receiving surface is called an R pixel; a photoelectric conversion device PD configured by arranging the green filter G on the light receiving surface is called a G pixel; a photoelectric conversion device PD configured by arranging the blue filter B on the light receiving surface is called a B pixel; and a photoelectric conversion device PD configured by arranging the cyan filter Cy on the light receiving surface is called a Cy filter.

Returning to the explanation with reference to FIG. 2, the explanation about the configuration of the imaging element 244 is continued.

Under the control of the imaging control unit 2446, the reading unit 2443 applies the driving pulse to the transfer transistors Tr11 to Tr14, so that the electrical charge is transferred from the photoelectric conversion device PD11 to PD14 to the charge-voltage conversion unit FD1. Then, under the control of the imaging control unit 2446, the reading unit 2443 supplies a power source voltage to the pixel output transistor $Tr_{AMP}$, so that the electrical signals that are voltage-converted by the charge-voltage conversion unit FD1 are output to the vertical signal line 291. Then, under the control of the imaging control unit 2446, the reading unit 2443 applies a reset pulse to the charge-voltage conversion reset transistor $Tr_{RST}$, and resets the charge-voltage conversion unit FD1 to a predetermined electrical potential. The reading unit 2443 is configured using a vertical scanning circuit and a horizontal scanning circuit.

Under the control of the imaging control unit 2446, the A/D conversion unit 2444 converts analog image data (electrical signals), which is input from the reading unit 2443, into digital electrical signals having a predetermined bit count, and outputs an image (captured image). For example, the A/D conversion unit 2444 performs conversion and obtains 10-bit digital image data (electrical signals), and outputs it to the outside. The A/D conversion unit 2444 is configured using an A/D conversion circuit.

The endoscope recording unit 2445 is used to record a variety of information related to the endoscope 2. For example, the endoscope recording unit 2445 is used to record identification information enabling identification of the endoscope 2, and to record identification information enabling identification of the imaging element 244. The endoscope recording unit 2445 is configured using a nonvolatile memory.

The imaging control unit 2446 controls the operations of the imaging element 244 based on an instruction signal input from the control device 5. More particularly, based on an instruction signal input from the control device 5, the imaging control unit 2446 controls the imaging frame rate and the imaging timing of the imaging element 244. More particularly, when an instruction signal indicating a normal observation mode is input from the control device 5, the imaging control unit 2446 sequentially outputs the electrical signals generated by the photoelectric conversion devices PD. On the other hand, when a mode for observation of a stroboscopic display in which the vocal cords of the subject undergo changes in quasi slow motion (hereinafter, called a "quasi-slow-motion observation mode") or when an instruction signal indicating a special observation mode is input, electrical signals generated by a plurality of Cy pixels are added on the basis of the filter units U1, and the addition result is output to the outside. For example, as a result of controlling the reading unit 2443, the imaging control unit 2446 applies a driving pulse to the transfer transistors Tr12 and Tr13 so that the electrical charge from the photoelectric conversion devices PD12 and PD13 is transferred to the charge-voltage conversion unit FD1 and the signal charge is added. Then, as a result of controlling the reading unit 2443, the imaging control unit 2446 transfers an added signal, which is obtained by the addition of the electrical signals of a plurality of CY pixels in the charge-voltage conversion unit FD1, to the vertical signal line 291. The imaging control unit 2446 is configured using a timing generator. As a result, the imaging element 244 becomes able to perform imaging at a higher frame rate than the vibrational frequency of the vocal cords of the subject. A higher frame rate than the vibrational frequency of the vocal cords of the subject is, for example, equal to 6000 fps. Meanwhile, when an instruction signal indicating the quasi-slow-motion observation mode or the special observation mode is input from the control device 5, the imaging control unit 2446 can make the imaging element 244 sequentially output the electrical signals generated by the photoelectric conversion devices PD present in a predetermined imaging region, so that the imaging is performed at a higher frame rate than the vibrational frequency of the vocal cords of the subject. Herein, the predetermined imaging region implies a region smaller than the imaging region in the normal observation mode.

The operating unit 22 includes the following: a bending knob 221 that makes the curved portion 25 bend in the vertical direction and the horizontal direction; a treatment tool insertion portion 222 through which a treatment tool such as medical forceps, a laser scalpel, or an inspection probe is inserted into the body cavity; and a plurality of switches 223 representing operation input units that receive input of an operation instruction signal regarding the peripheral devices including not only the light source device 3 and the control device 5 but also an insufflation unit, a water supply unit, and a gas supply unit, or receive input of a pre-freeze signal as an instruction for the imaging element 244 to perform still image photographing. The treatment tool inserted from the treatment tool insertion portion 222 passes through a treatment tool channel (not illustrated) in the front end portion 24 and comes out from an opening (not illustrated) of the front end portion 24.

The universal cord 23 has at least the light guide 241 and a cable assembly, which has one of more cables bundled therein, built-in. The cable assembly represents signal lines for sending and receiving signals among the endoscope 2, the light source device 3, and the control device 5; and includes a signal line for sending and receiving setting data, a signal line for sending and receiving image data, and a signal line for sending and receiving driving clock signals meant for driving the imaging element 244. The universal cord 23 includes a connector unit 27 that is detachably attachable to the light source device 3. The connector unit 27 has a coil cable 27a extending in a coiled manner, and includes a connector unit 28 that is positioned at the extended end of the coil cable 27a and that is detachably attachable to the control device 5.

Configuration of Light Source Device

Given below is the explanation of a configuration of the light source device 3.

The light source device 3 supplies an illumination light from the front end portion 24 of the endoscope 2 for the purpose of illuminating the subject. The light source device 3 includes a light source unit 31, a light source driver 32, and an illumination control unit 33.

The light source unit 31 irradiates the subject with an illumination light including either the light having the wavelength bandwidth of the red color or the light having the wavelength bandwidth of the blue color, and including the light having the wavelength bandwidth of the green color; or irradiates the subject with a special light including the light having the wavelength bandwidth of the green color, and including a narrow-bandwidth light (for example, the wavelength bandwidth of 415 nm to 540 nm). The light source unit 31 includes a condenser lens 311, a first light source 312, a second light source 313, a third light source 314, and a fourth light source 315.

The condenser lens 311 is configured using one or more lenses. The condenser lens 311 collects the light emitted from the first light source 312, the second light source 313, the third light source 314, and the fourth light source 315; and sends the collected light to the light guide 241.

The first light source 312 is configured using a red LED lamp (LED stands for Light Emitting Diode). Based on the electric current supplied from the light source driver 32, the first light source 312 emits the light having the wavelength bandwidth of the red color (hereinafter, simply referred to as "R light").

The second light source 313 is configured using a green LED lamp. Based on the electric current supplied from the light source driver 32, the second light source 313 emits the light having the wavelength bandwidth of the green color (hereinafter, simply referred to as "G light").

The third light source 314 is configured using a blue LED lamp. Based on the electric current supplied from the light source driver 32, the third light source 314 emits the light having the wavelength bandwidth of the blue color (hereinafter, simply referred to as "B light").

The fourth light source 315 is configured using a violet LED lamp. Based on the electric current supplied from the light source driver 32, the fourth light source 315 emits the light having the wavelength bandwidth of the violet color (for example, 415 nm±10) (hereinafter, simply referred to as "V light").

Under the control of the illumination control unit 33, the light source driver 32 supplies an electric current to the first light source 312, the second light source 313, and the third light source 314, so that the lights are emitted according to the observation mode set in the imaging system 1. More particularly, if the normal observation mode is set in the imaging system 1; then, under the control of the illumination control unit 33, the light source driver 32 makes the first light source 312, the second light source 313, and the third light source 314 emit light, so that the white light gets emitted (simultaneous formula). Moreover, if the special light observation mode is set in the imaging system 1; then, under the control of the illumination control unit 33, the light source driver 32 makes the second light source 313 and the fourth light source 315 emit light, so that a narrow-bandwidth light gets emitted.

Based on the instruction signal received from the control device 5, the illumination control unit 33 controls the lighting-up timing of the light source device 3. More particularly, the illumination control unit 33 makes the first light source 312, the second light source 313, and the third light source 314 emit light at predetermined periodicity. The illumination control unit 33 is configured using a processor that is a processing device having a hardware component such as a central processing unit (CPU), and using a memory representing a temporary memory area used by the processor. Moreover, when the special light observation mode is set as the observation mode in the imaging system 1, the illumination control unit 33 controls the light source driver 32 and makes the second light source 313 and the fourth light source 315 in combination, so that a narrow-bandwidth light is emitted. Furthermore, when the quasi-slow-motion observation mode is set as the observation mode in the imaging system 1, the illumination control unit 33 controls the light source driver 32 and makes the second light source 313 and the third light source 314 emit light on a constant basis, so that the white light is constantly emitted. Meanwhile, according to the observation mode set in the imaging system 1, the illumination control unit 33 can control the light source driver 32 and make any two or more of the first light source 312, the second light source 313, the third light source 314, and the fourth light source 315 emit light in combination.

Configuration of Display Device

Given below is the explanation of a configuration of the display device 4.

The display device 4 displays a display image based on the image data that is generated by the endoscope 2 and that is received from the control device 5. Moreover, the display device 4 displays a variety of information related to the imaging system 1. The display device 4 is configured using a liquid crystal display panel or an organic electroluminescence (organic EL) display panel.

Configuration of Control Device

Given below is the explanation of a configuration of the control device 5.

The control device 5 receives image data generated by the endoscope 2, performs predetermined image processing with respect to the received image data, and outputs the processed image data to the display device 4. The control device 5 includes a detecting unit 51, a calculating unit 52, a determining unit 53, an input unit 54, a setting unit 55, a selecting unit 56, an image processing unit 57, a recording unit 58, and a processing control unit 59. In the first embodiment, the control device 5 functions as an image processing device.

The detecting unit 51 detects the vibrational frequency of the vocal cords of the subject based on a plurality of images generated at an imaging frame rate of a higher frequency than the vibrational frequency of the vocal cords of the subject and that is input from the endoscope 2. More particularly, the detecting unit 51 treats a plurality of images, which are received from the endoscope 2, as input data; estimates the vibrational frequency of the vocal cords as output data; and outputs the output data. The detecting unit 51 is configured using a processor that is a processing device having a hardware component such as a graphics processing unit (GPU), and using a memory representing a temporary memory area used by the processor. For example, the detecting unit 51 is implemented using a learning model that performs machine learning using, as teacher data, a plurality of images and videos of the vocal cords of a plurality of subjects previously captured for each band frequency of the vocal cords of the plurality of subjects; and outputs, as the output, the vibrational frequency of the vocal cords of the concerned subject. Herein, there is no restriction on the type of machine learning. For example, teacher data or learning data can be provided in which the vibrational frequency of the vocal cords is linked with still images in which the condition of the vocal cords is captured, and the learning can be performed by inputting the teacher data or the learning data in a calculation model that is based on a multilayered neural network. Moreover, as a machine learning method, for example, it is possible to implement a method based on a deep neural network (DNN) of a multilayered neural network such as a convolutional neural network (CNN) or a 3D-CNN. Furthermore, when time-series data such as a video in the form of video data is treated as the target; then, as a machine learning method, it is possible to implement a method based on recurrent neural network (RNN) or based on long short-term memory (LSTM) units obtained as a result of expanding an RNN.

Based on the vibrational frequency of the vocal cords of the subject as sequentially input from the detecting unit 51, the calculating unit 52 calculates the variation in the vibrational frequency of the vocal cords. For example, based on the vibrational frequency of the vocal cords of the subject as sequentially input from the detecting unit 51, the calculating unit 52 calculates the second-by-second variation in the vibrational frequency of the vocal cords of the subject. The calculating unit 52 is configured using a processor that is a processing device having a hardware component such as a central processing unit (CPU), and using a memory representing a temporary memory area used by the processor.

The determining unit 53 determines whether or not the variation calculated by the calculating unit 52 is equal to or greater than a threshold value. The threshold value enables distinguishing between a low-pitch sound and a high-pitch sound. Meanwhile, the determining unit 53 can be installed for each sound range, so that the variation can be determined according to the corresponding threshold value.

The input unit 54 receives input corresponding to a user operation, and outputs a signal corresponding to the received user operation to the setting unit 55 or the processing control unit 59. Moreover, the input unit 54 receives input of an instruction signal indicating the selection period (sampling period) set by the setting unit 55 (explained later), and outputs the instruction signal to the setting unit 55. Moreover, the input unit 54 receives input of an instruction signal indicating the phase variation of each display cycle (explained later) that is preset and is displayed in the display device 4; and outputs the instruction signal to the setting unit 55. The input unit 54 is configured using switches, buttons, a touch-sensitive panel, or a jog dial.

Based on the vibration period of the vocal cords of the subject as detected by the detecting unit 51, based on the imaging frame rate of the imaging element 244, based on the display frame rate of the display device 4, and based on the variation in the phase of each display cycle that is preset for display purpose in the display device 4; the setting unit 55 sets a selection period (sampling period) that enables the selecting unit 56 (explained later) select, at a longer interval than the vibration period of the vocal cords of the subject, an image that, from among a plurality of images, is to be displayed in the display device 4. More particularly, the setting unit 55 sets the selection period (sampling period) for the selecting unit 56 (explained later) based on the following: an instruction signal indicating the selection period as input from the input unit 54; the display frame rate of the display device 4 as input from the processing control unit 59; the imaging frame rate of the imaging element 244; and the phase variation of each display cycle that is preset for display purpose in the display device 4. Moreover, based on an instruction signal input from the input unit 54, the setting unit 55 sets a phase variation $\beta(\theta)$ to be equal to or greater than 0° and smaller than 90° (i.e., to satisfy $0° \leq \theta < 90°$). Furthermore, if the determining unit 53 determines that the variation is equal to or greater than the threshold value, then the setting unit 55 varies the selection period for the selecting unit 56. The setting unit 55 is configured using a processor that is a processing device having a hardware component such as a central processing unit (CPU), and using a memory representing a temporary memory area used by the processor.

The selecting unit 56 sequentially selects, from among a plurality of images generated in the endoscope 2 that includes the imaging element 244 capable of performing imaging at a higher frequency than the vibrational frequency of the vocal cords of the subject, the images to be displayed in the display device 4 based on the selection period that is longer than the vibration period of the vocal cords of the subject; and outputs each selected image to the image processing unit 57. More particularly, the selecting unit 56 sequentially selects, from among a plurality of images generated by the imaging element 244 of the endoscope 2, images to be displayed in the display device 4 based on the selection period that is set by the setting unit 55 and that is longer than the vibration period of the vocal cords of the subject; and outputs each selected image to the image processing unit 57. More particularly, based on the selection period set by the setting unit 55, from among a plurality of images generated by the imaging element 244 of the endoscope 2, the selecting unit 56 performs selection by thinning out the images that are not to be displayed in the display device 4; and outputs the selected images. The selecting unit 56 is configured using a processor that is a processing device having a hardware component such as a central processing unit (CPU), and using a memory representing a temporary memory area used by the processor.

The image processing unit 57 performs a variety of image processing with respect to the image input thereto from the selecting unit 56 and generates a display image, and outputs the display image to the display device 4. The image processing includes de-mosaicing, γ correction, noise reduction, white balance adjustment, and structure enforcement. The image processing unit 57 is configured using a processor that is a processing device having a hardware component such as a graphics processing unit (GPU) or a field programmable gate array (FPGA), and using a memory representing a temporary memory area used by the processor.

The recording unit 58 is used to record: a variety of information related to the imaging system 1; the information being processed; computer programs; and images. The recording unit 58 is configured using a read only memory (ROM), a random access memory (RAM), a hard disk drive (HDD), a solid state drive (SSD), or a recording medium. The recording unit 58 includes a program recording unit 581 used to store various computer programs to be executed in the imaging system 1; and an image recording unit 582 used to record a plurality of images generated by the imaging element 244 of the endoscope 2 or a video made from the images generated by the imaging element 244 of the endoscope 2.

The processing control unit 59 comprehensively controls the constituent elements of the imaging system 1, and controls various operations. The processing control unit 59 is configured using a processor that is a processing device having a hardware component such as a CPU, or an FPGA, or an application specific integrated circuit (FPGA), and using a memory representing a temporary memory area used by the processor. Meanwhile, the calculating unit 52, the determining unit 53, the setting unit 55, the selecting unit 56, and the image processing unit 57 can be implemented using a single hardware component.

Overview of Conventional Observation Method for Observing Vocal Cords of Subject Given below is the explanation of a conventional observation method for observing the vocal cords of the subject.

FIG. 6 is a diagram that schematically illustrates the overview of the conventional observation method for observing the vocal cords of the subject. In FIG. 6, the vertical axis represents the amplitude of the vibrations of the vocal cords, and the horizontal axis represents the time. Moreover, in FIG. 6, a curved line L10 represents the schematically-expressed vibrational frequency of the vocal cords, and filled circles P1 represent the imaging timings preset based on the vibrational frequency of the vocal cords.

As indicated by the filled circles P1 in FIG. 6, in the conventional observation method for observing the vocal cords of the subject (hereinafter, referred to as the "conventional observation method"), the vibrational frequency of the vocal cords is detected using a microphone; and, based on the detected vibrational frequency of the vocal cords, imaging is performed while sequentially emitting an illumination light at imaging timings preset. As a result, a plurality of images is generated. Then, in the conventional observation method, after temporarily recording them in the memory, the images are reproduced in chronological order and in slow motion. Hence, in the conventional observation method, the vocal cords of the subject cannot be observed in real time. Moreover, in the endoscope used in the conventional observation method, not only a microphone is required to detect the vibrational frequency of the vocal cords of the subject, there is also a lack of general versatility.

Overview of Observation Method for Observing Vocal Cords of Subject

Figure 7:
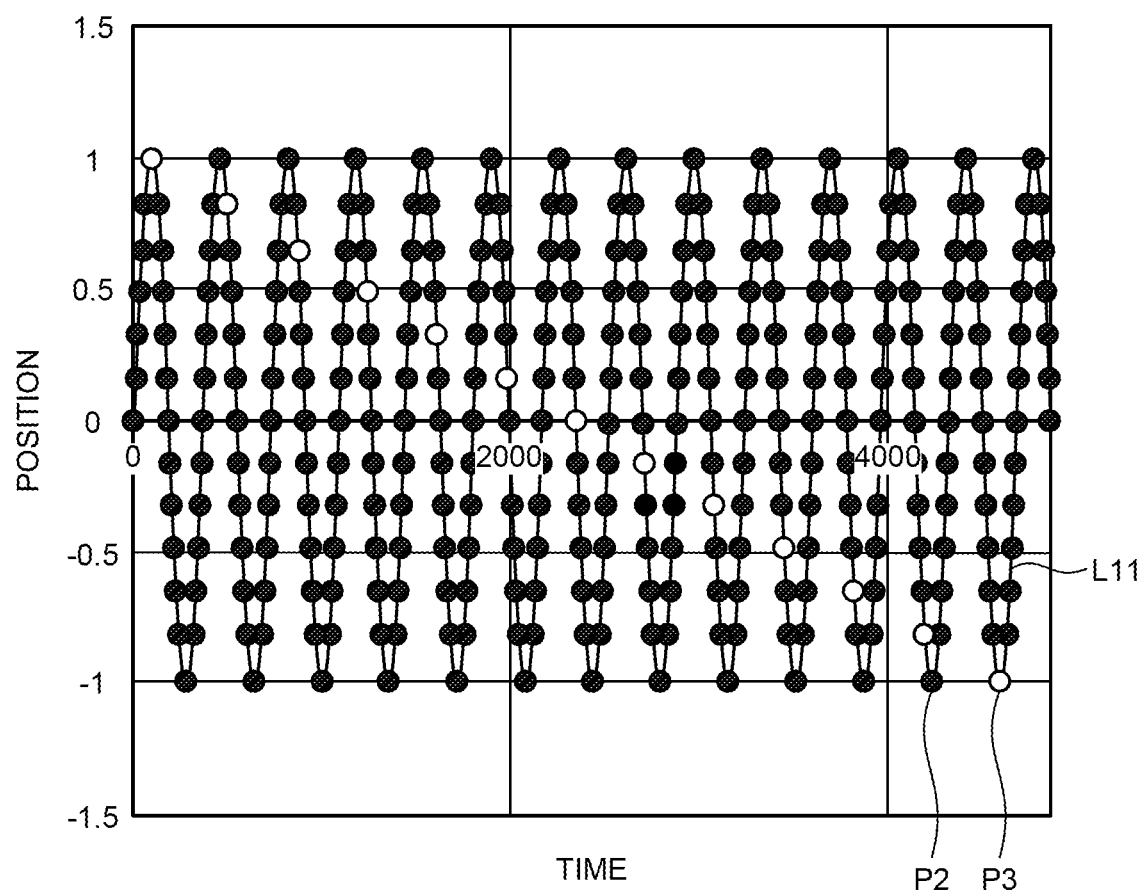
FIG. 7 is a diagram that schematically illustrates the overview of an observation method for observing a subject according to the first embodiment.

Given below is the explanation of an observation method for observing the vocal cords of the subject according to the first embodiment. FIG. 7 is a diagram that schematically illustrates the overview of the observation method for observing the vocal cords of the subject according to the first embodiment. In FIG. 7, the vertical axis represents the amplitude of the vibrations of the vocal cords, and the horizontal axis represents the time. Moreover, in FIG. 7, a curved line L11 represents the schematically-expressed vibrational frequency of the vocal cords. Moreover, filled circles P2 represent the imaging timings at which imaging is performed according to predetermined imaging frames; and white circles P3 represent the images selected by the selecting unit 56 from among a plurality of images.

As illustrated in FIG. 7, regardless of the vibrational frequency of the vocal cords, the imaging element 244 performs high-speed imaging at the imaging frame rate (for example, 6000 fps) having a higher frequency than the vibrational frequency of the vocal cords. Then, from among a plurality of images generated in real time by the imaging element 244, the selecting unit 56 sequentially selects images, which are to be displayed in the display device 4, based on the selection period set by the setting unit 55; and outputs each selected image to the image processing unit 57. Subsequently, the image processing unit 57 performs image processing with respect to the images that are sequentially input from the selecting unit 56, and outputs each processed image to the display device 4. As a result, the display device 4 can display, in real time and in quasi slow motion, the changes occurring in the vocal cords of the subject. As a result, the user such as a doctor becomes able to observe the vocal cords of the subject in real time. Moreover, in the imaging system 1, since no separate microphone needs to be installed for detecting the vocal cords, a simple configuration with a high degree of general versatility can be achieved.

Overview of Quasi-Slow-Motion Observation Mode

Given below is the explanation of the quasi-slow-motion observation mode explained with reference to FIG. 7. FIG.

Figure 8:
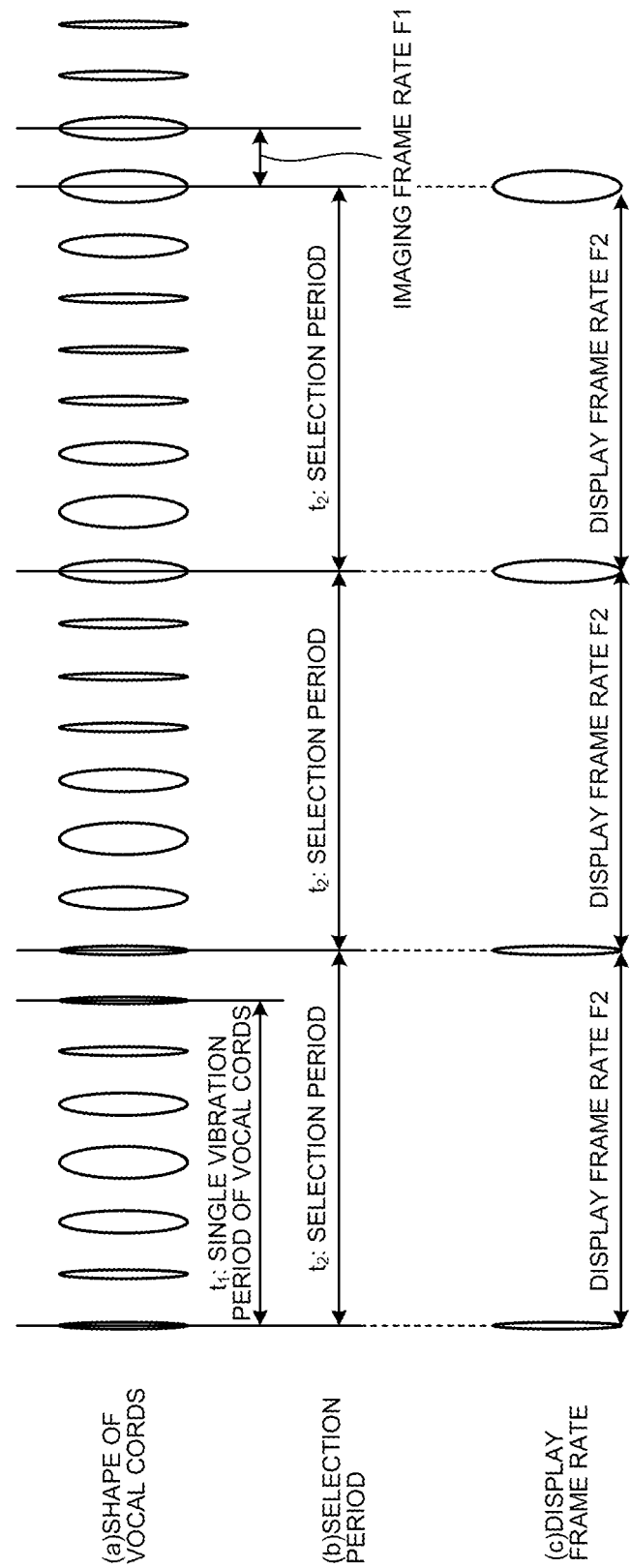

8 is a diagram that schematically illustrates the overview of the quasi-slow-motion observation mode. In FIG. 8, from the top, (a) schematically represents the changes in the condition of the vocal cords of the subject; (b) represents the selection period set by the setting unit 55; and (c) schematically represents the condition of the vocal cords that is selected for display by the selecting unit 56 from among a plurality of images. In FIG. 8, in order to simplify the explanation, the vocal cords captured in an image are picked out and are schematically expressed. However, in the actual images, the form of the vocal cords undergoes changes within each image.

As illustrated in FIG. 8, based on the selection period set by the setting unit 55, from among a plurality of images generated by the imaging element 244 of the endoscope 2 at a higher frequency than the vibrational frequency of the vocal cords, the selecting unit 56 sequentially selects images based on the selection period that is longer than the vibration period of the vocal cords, and outputs the selected images to the display device 4 via the image processing unit 57. As a result, as illustrated in (c) in FIG. 8, the display device 4 can display, in quasi slow motion, the display images in which the condition of the vocal cords undergoes changes. In that case, based on a plurality of images generated by the imaging element 244 at a higher frequency than the vibrational frequency of the vocal cords, the detecting unit 51 detects the vibration period or the vibrational frequency of the vocal cords. Then, based on the vibration period of the vocal cords as detected by the detecting unit 51 and based on an instruction signal input from the input unit 54, the setting unit 55 sets a selection period $t_2$ (sampling period), which enables the selecting unit 56 to select an image from among a plurality of images, according to Equation (1) given below.

$$t_2 = \alpha \times t_1 + \beta \quad (1)$$

Herein, $\alpha$ represents an integer equal to or greater than 1; and $\beta$ is a value previously specified by the user via an instruction signal input from the input unit 54, and represents the phase variation of each display cycle displayed in the display device 4.

In this way, based on the selection period $t_2$ set by the setting unit 55 according to Equation (1), from among a plurality of images generated by the imaging element 244 of the endoscope 2 at a higher frequency than the vibrational frequency of the vocal cords, the selecting unit 56 sequentially selects images based on the selection period that is longer than the vibration period of the vocal cords, and outputs each selected image to the image processing unit 57. As a result, even when there is fluctuation in the vibrational frequency of the vocal cords, the display device 4 becomes able to display the fast-moving vocal cords in slow motion.

Setting Method of Selection Period $t_2$

Figure 9:
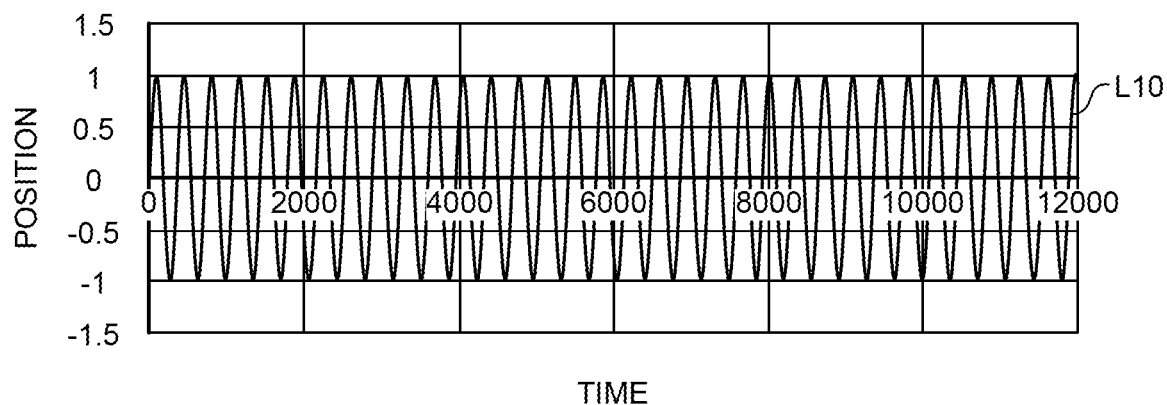
FIG. 9 is a diagram that schematically illustrates the overview of a quasi-slow-motion observation mode.
Figure 10:
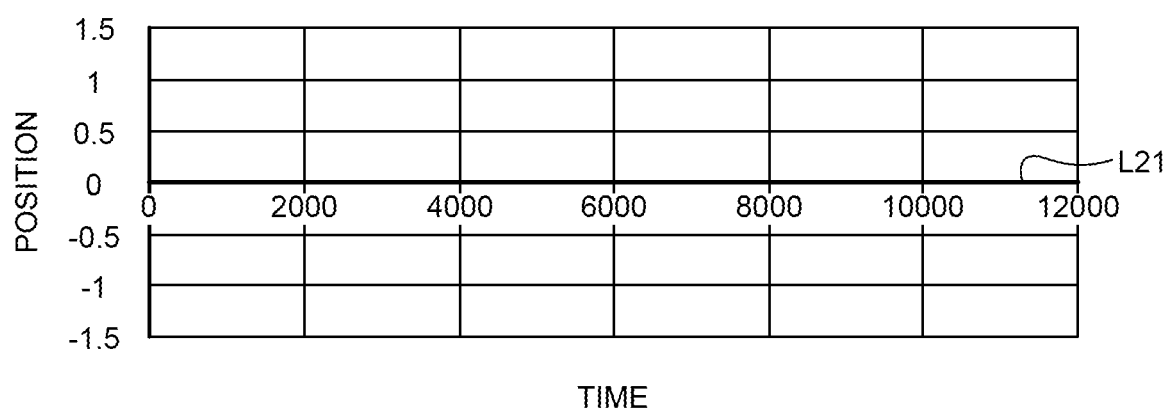
FIG. 10 is a diagram that schematically illustrates an example of a selection period set by a setting unit.
Figure 11:
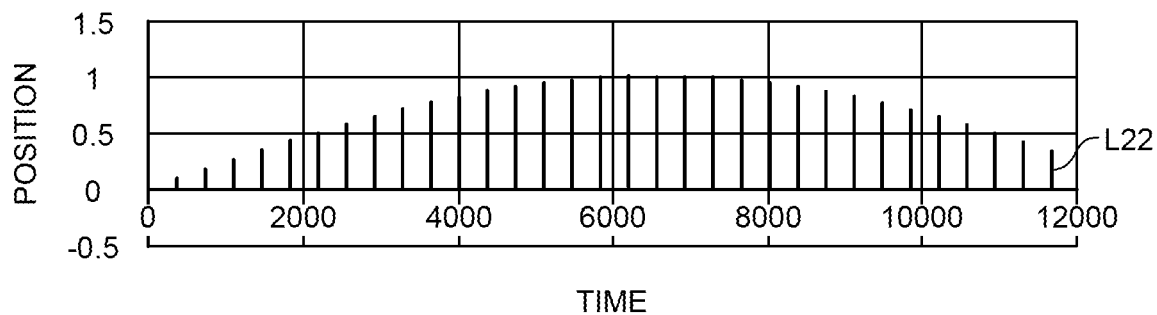
FIG. 11 is a diagram that schematically illustrates another example of the selection period set by the setting unit.
Figure 12:
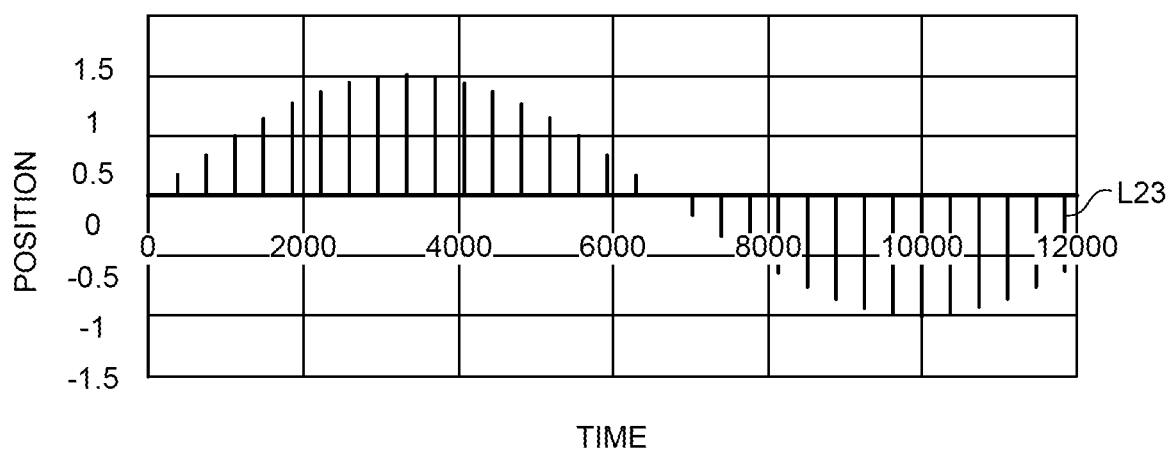
FIG. 12 is a diagram that schematically illustrates still another example of the selection period set by the setting unit.
Figure 13:
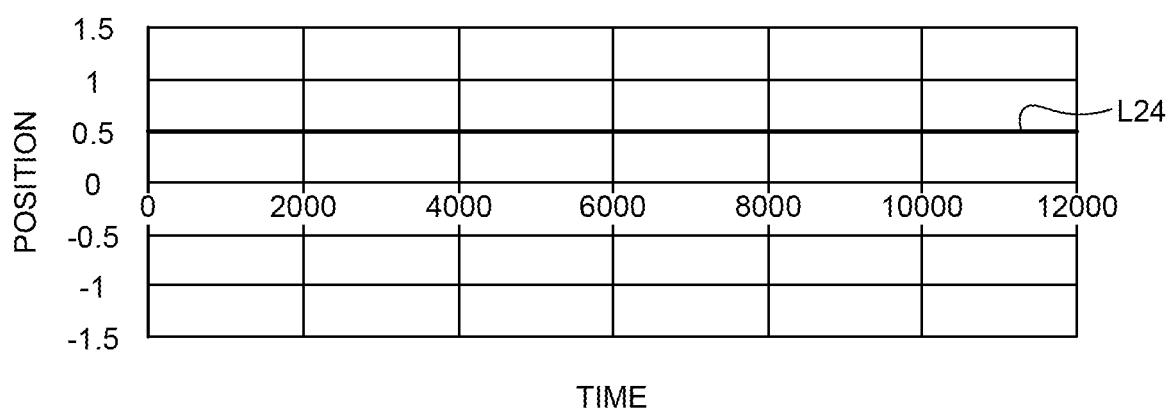
FIG. 13 is a diagram that schematically illustrates still another example of the selection period set by the setting unit.

Given below is the detailed explanation about the selection period $t_2$ set by the setting unit 55. FIG. 9 is a diagram that schematically illustrates the vibrational frequency of the vocal cords of the subject. FIG. 10 is a diagram that schematically illustrates an example of the selection period set by the setting unit 55. FIG. 11 is a diagram that schematically illustrates another example of the selection period set by the setting unit 55. FIG. 12 is a diagram that schematically illustrates still another example of the selection period set by the setting unit 55. FIG. 13 is a diagram that schematically illustrates still another example of the selection period set by the setting unit 55. In FIG. 9, the curved line L10 represents the vibrational frequency of the vocal cords. In FIG. 10, a case is illustrated in which $\alpha=100$ and $\beta=0$ is set by the setting unit 55, and a curved line L21 represents the vibrational frequency of the vocal cords. In FIG. 11, a case is illustrated in which $\alpha=100$ and $\beta=5°$ is set by the setting unit 55, and a curved line L22 represents the vibrational frequency of the vocal cords. In FIG. 12, a case is illustrated in which $\alpha=100$ and $\beta=6=10°$ is set by the setting unit 55, and a curved line L23 represents the vibrational frequency of the vocal cords. In FIG. 13, a case is illustrated in which, when $\alpha=100$ and $\rho=0$ is set by the setting unit 55, the initial phase of the selection period is set to $\gamma$ using the input unit 54; and a curved line L24 represents the vibrational frequency of the vocal cords. In FIGS. 9 to 13, the horizontal axis represents the time, and the vertical axis represents the amplitude.

As illustrated in FIGS. 9 and 10, when the setting unit 55 sets the phase variation $\beta$ in the selection period $t_2$ to 0 ($\beta=0$), the selecting unit 56 displays a selected still image of a particular state of the phase from among a plurality of images. The setting unit 55 sets the selection period $t_2$ in such a way that the integer $\alpha$ approaches the display frame rate. For example, if the imaging element 244 has the imaging frame rate of 6000 fps and if the display device 4 has the display frame rate of 60 fps; then the setting unit 55 sets the integer $\alpha$ to 100 because $600 \div 60 = 100$ holds true. As a result, the selecting unit 56 can select, from among a plurality of images, the frames of images at the interval of $\frac{1}{100}$-th of the imaging period and output them to the display device 4. Hence, the display device 4 becomes able to display the display images at the interval of $\frac{1}{100}$-th of the imaging period. Meanwhile, the imaging frame rate of the imaging element 244 needs to be sufficiently faster than the vibration period (of, for example, $\frac{1}{200}$ seconds) of the vocal cords. For example, the imaging frame rate is equal to 6000 fps.

Given below is the detailed explanation about the phase variation $\beta$ set by the setting unit 55. The phase variation in each display cycle of a display image displayed in the display device 4 can be expressed according to Equation (2) given below.

$$2\pi\beta/t_1 = \theta \quad (2)$$

Thus, when the setting unit 55 sets the phase variation $\beta$ to 0 ($\beta=0$); according to Equation (1), the image that is selected as the display image by the selecting unit 56 from among a plurality of images does not undergo any shift in the phase and becomes a still image.

In a display image in the form of a still image displayed in the display device 4, unless there is any change in the vocal cords captured therein, the user such as a doctor is not able to observe the condition of the vocal cords. Hence, the setting unit 55 sets the phase variation $\beta$ to a value greater than 0, so that the display image displayed in the display device 4 undergoes a shift in the phase in each display frame. More particularly, the setting unit 55 sets the phase variation $\beta$ under condition (3) given below.

$$0 < \beta < t_1 \quad (3)$$

As a result, based on the selection period $t_2$ set by the setting unit 55, the selecting unit 56 selects a display image from among a plurality of images and outputs it to the display device 4. As a result, as indicated by the curved line L22 in FIG. 11 and the curved line L23 in FIG. 12, such a display image can be selected which undergoes a change in the phase in each display frame of the display device 4.

In this way, the setting unit 55 sets the value a according to the display frame displayed in the display device 4; and sets the phase variation $\beta$ for slow motion based on an instruction signal that is input from the input unit 54 and that indicates the phase variation of each display cycle displayed in the display device 4. Then, the selecting unit 56 becomes able to select display images for quasi slow motion from among a plurality of images obtained as a result of performing high-speed imaging based on the selection period $t_2$ set by the setting unit 55.

Moreover, as indicated by a straight line L24 in FIG. 13, when the phase variation β is set to 0, if an instruction signal is input from the input unit 54 as an instruction for varying the initial phase of the selection period, the setting unit 55 varies the initial phase γ of the selection period ($t_2=(\alpha \times t_1 + \beta)+\gamma$) according to the instruction signal. As a result, the user such as a doctor becomes able to observe the condition of the vocal cords by stopping the changes therein at the desired state.

Operations in Imaging System

Figure 14:
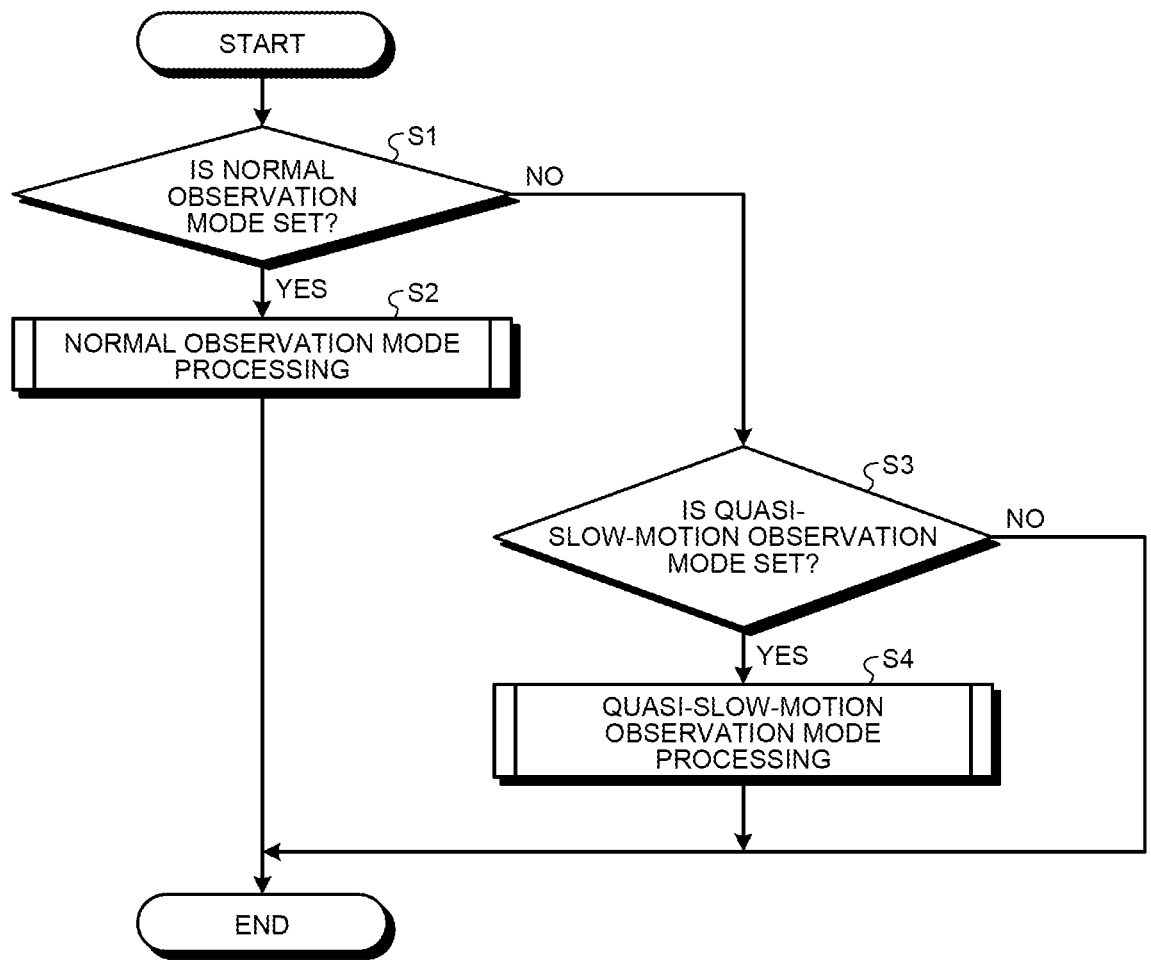
FIG. 14 is a flowchart for explaining the overview of the operations performed in the imaging system.

Given below is the explanation about the operations performed in the imaging system 1. FIG. 14 is a flowchart for explaining the overview of the operations performed in the imaging system 1.

As illustrated in FIG. 14, firstly, the explanation is given about the case in which the normal observation mode is set in the imaging system 1 (Yes at Step S1). In that case, the imaging system 1 performs normal observation mode processing in which sequential imaging is performed at a predetermined imaging frame rate, and images are displayed (Step S2). After the operation at Step S2 is performed, the imaging system 1 ends the operations. Regarding the normal observation mode processing, the detailed explanation is given later.

The following explanation is given about the case in which, at Step S1, the normal observation mode is not set in the imaging system 1 (No at Step S1). In that case, the system control proceeds to Step S3.

If the quasi-slow-motion observation mode is set in the imaging system 1 (Yes at Step S3), then the imaging system 1 performs quasi-slow-motion observation mode processing in which the vocal cords of the subject are observed in real time and in slow motion in quasi manner (Step S4). After the operation at Step S4 is performed, the imaging system 1 ends the operations. Regarding the quasi-slow-motion observation mode processing, the detailed explanation is given later.

Meanwhile, at Step S3, if the quasi-slow-motion observation mode is not set in the imaging system 1 (No at Step S3), then the imaging system 1 ends the operations.

Overview of Normal Observation Mode Processing

Figure 15:
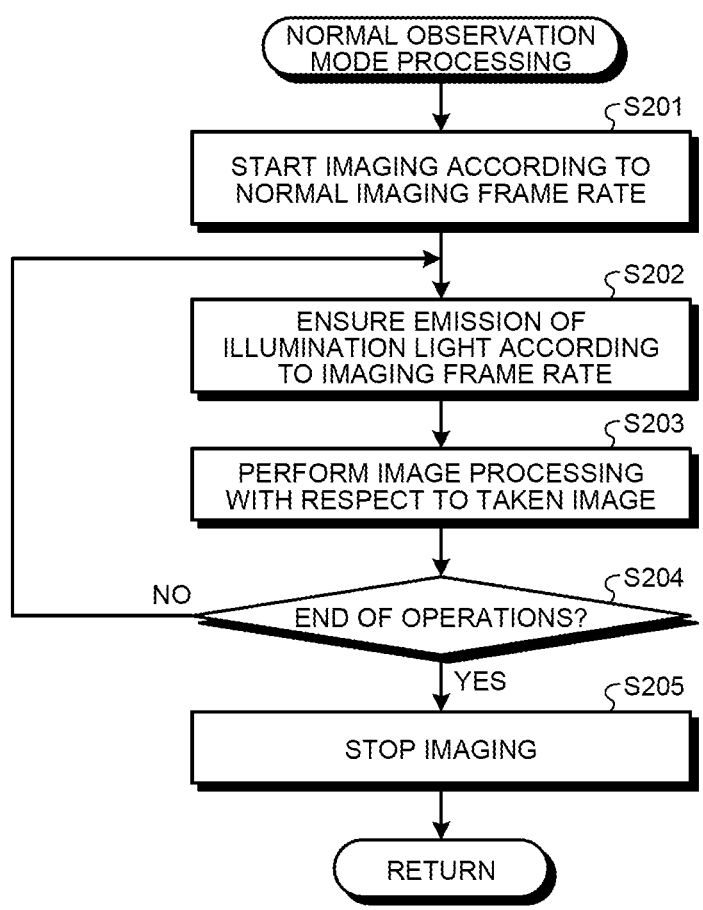
FIG. 15 is a flowchart for explaining the overview of normal observation mode processing.

Given below is the detailed explanation of the normal observation mode processing performed at Step S2. FIG. 15 is a flowchart for explaining the overview of the normal observation mode processing.

As illustrated in FIG. 15, firstly, the processing control unit 59 makes the imaging element 244 start the imaging at the normal imaging frame rate (Step S201). More particularly, the processing control unit 59 makes the imaging element 244 start the imaging at 60 fps.

Then, the processing control unit 59 makes the light source device 3 emit the illumination light according to the imaging frame rate (Step S202). In that case, the first light source 312, the second light source 313, and the third light source 314 of the light source device 3 emit lights in synchronization with the imaging frame rate, so that the white illumination light is supplied to the endoscope 2.

Subsequently, the image processing unit 57 performs image processing with respect to the image (captured image) input via the selecting unit 56, and outputs the processed image to the display device 4 (Step S203). As a result, the display device 4 displays the display image based on the image (captured image) input from the image processing unit 57. In that case, the selecting unit 56 outputs, without selection and to the image processing unit 57, a plurality of images (captured images) from the imaging element 244 of the endoscope 2.

Then, if an instruction signal is input from the input unit 54 as an instruction to end the observation (Yes at Step S204), the processing control unit 59 stops the imaging being performed by the imaging element 244 (Step S205). After the operation at Step S205 is performed, the system control returns to the main routine explained earlier with reference to FIG. 14, and the present operations are ended.

At Step S204, if an instruction signal indicating an instruction to end the observation is not input from the input unit 54 (No at Step S204), then the system control returns to Step S202.

Overview of Quasi-Slow-Motion Observation Mode Processing

Figure 16:
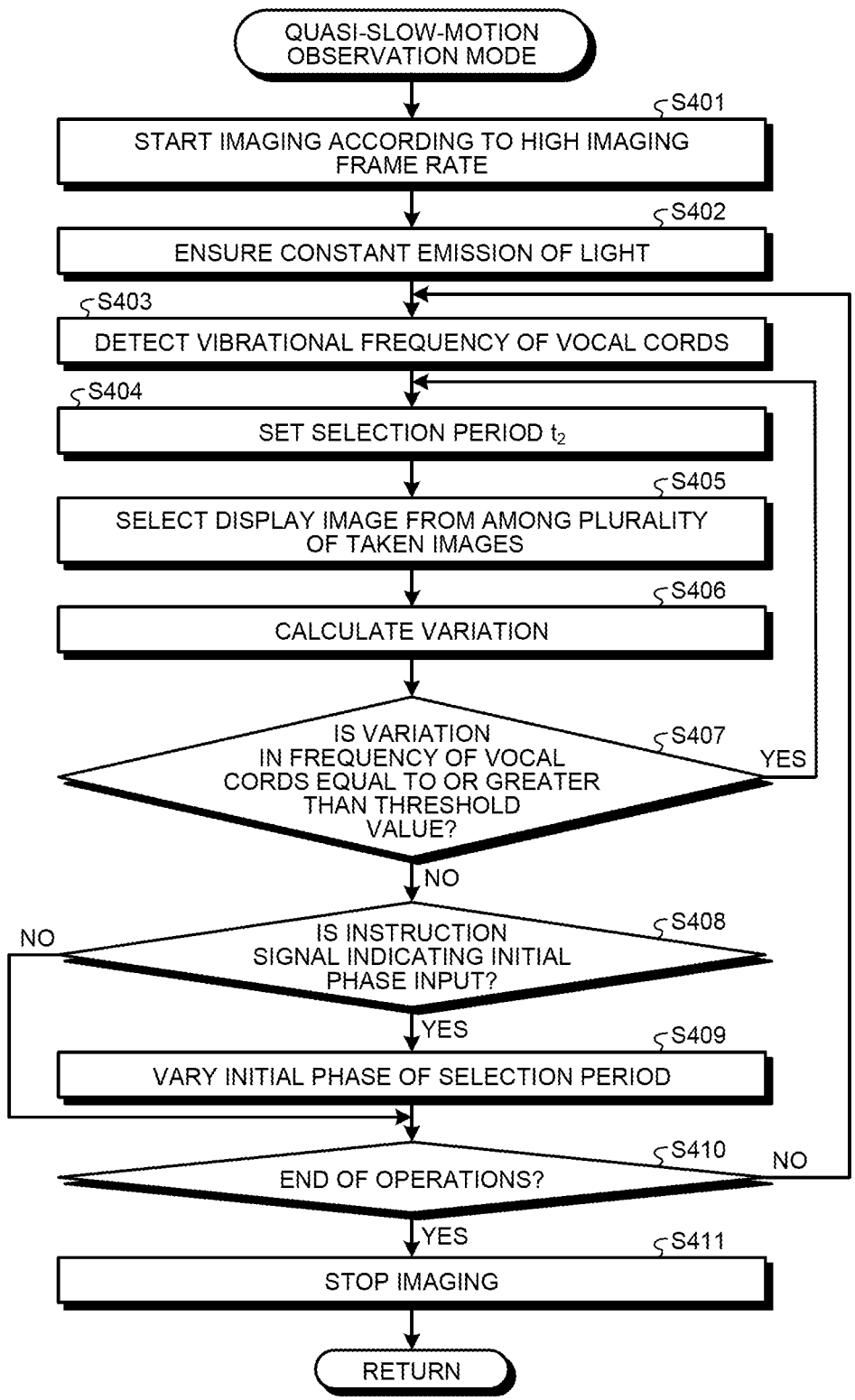
FIG. 16 is a flowchart for explaining the overview of quasi-slow-motion observation mode processing.

Given below is the detailed explanation of the quasi-slow-motion observation mode processing performed at Step S4. FIG. 16 is a flowchart for explaining the overview of the quasi-slow-motion observation mode processing.

As illustrated in FIG. 16, firstly, the processing control unit 59 makes the imaging element 244 start the imaging at a high imaging frame rate (Step S401).

Then, the processing control unit 59 makes the light source device 3 emit light on a constant basis (Step S402). More particularly, the first light source 312, the second light source 313, and the third light source 314 of the light source device 3 emit light on a constant basis.

Subsequently, based on a plurality of images input from the imaging element 244, the detecting unit 51 detects the vibrational frequency of the vocal cords of the subject (Step S403).

Then, the setting unit 55 sets the selection period for the selecting unit 56 (Step S404). More particularly, the setting unit 55 sets the selection period $t_2$ based on the display frame rate of the display device 4, based on the imaging frame rate of the imaging element 244, and based on an instruction signal previously input from the input unit 54 as an instruction about the phase variation (β).

Subsequently, based on the selection period $t_2$ set by the setting unit 55, the selecting unit 56 selects, as the display image to be displayed in the display device 4, a display image from among a plurality of images (captured images) input from the imaging element 244 (Step S405).

Then, the calculating unit 52 calculates the variation in the vibrational frequency of the vocal cords of the subject as detected by the detecting unit 51 (Step S406).

Subsequently, the determining unit 53 determines whether or not the variation calculated by the calculating unit 52 is equal to or greater than a threshold value (Step S407). If the determining unit 53 determines that the variation calculated by the calculating unit 52 is equal to or greater than the threshold value (Yes at Step S407), then the system control returns to Step S404. In that case, the setting unit 55 sets the selection period $t_2$ by varying it based on the display frame rate of the display device 4, based on the imaging frame rate of the imaging element 244, based on an instruction signal previously input from the input unit 54 as an instruction about the phase variation (β), and based on the variation calculated by the calculating unit 52. That enables performing display by conforming with the vibrational frequency of the vocal cords of the subject.

On the other hand, at Step S407, if the determining unit 53 determines that the variation calculated by the calculating unit 52 is not equal to or greater than the threshold value (No at Step S407), then the system control proceeds to Step S408.

At Step S408, when an instruction signal indicating the initial phase γ is input from the input unit 54 (Yes at Step S408), the setting unit 55 varies the initial phase of the selection period for the selecting unit 56 to the initial phase specified in the instruction signal that is input from the input unit 54 (Step S409). As a result, the display device 4 becomes able to display the display image in which the captured shape of the vocal cords is as desired by the user such as a doctor. After the operation at Step S409 is performed, the system control proceeds to Step S410 (explained later).

Meanwhile, at Step S408, if an instruction signal indicating the initial phase γ has not been input from the input unit 54 (No at Step S408), then the system control proceeds to Step S410 (explained later).

Subsequently, if an instruction signal is input from the input unit 54 as an instruction to end the observation (Yes at Step S410), then the processing control unit 59 stops the imaging being performed by the imaging element 244 (Step S411). After the operation at Step S411 is performed, the system control returns to the main routine illustrated in FIG. 14. That marks the end of the operations explained with reference to FIG. 16. On the other hand, if an instruction signal indicating an instruction to end the observation is not input from the input unit 54 (No at Step S410), then the system control returns to Step S403.

According to the first embodiment explained above, from among a plurality of images (captured images) generated in the endoscope 2 that includes the imaging element 244 which is capable of performing imaging at a longer frequency than the vibrational frequency of the vocal cords of the subject representing a photographic subject; the selecting unit 56 sequentially selects, based on the selection period that is longer than the vibration period of the vocal cords of the subject, images to be displayed in the display device 4; and outputs each selected image to the display device 4 via the image processing unit 57. As a result, it becomes possible to observe the vocal cords of the subject in real time.

Moreover, according to the first embodiment, the detecting unit 51 detects the vibrational frequency of the vocal cords of the subject based on a plurality of images input from the endoscope 2. Hence, no separate microphone needs to be installed for detecting the vocal cords, thereby enabling achieving a simple configuration with a high degree of general versatility.

Moreover, according to the first embodiment, based on the vibration period of the vocal cords of the subject, based on the imaging frame rate of the imaging element 244, based on the display frame rate of the display device 4, and based on the phase variation in each display cycle that is preset for display purpose in the display device 4; the setting unit 55 sets the selection period that enables the selecting unit 56 to perform selection. As a result, the user such as a doctor becomes able to observe the vocal cords at the desired change rate and in the desired state of the vocal cords.

Furthermore, according to the first embodiment, since the setting unit 55 sets the phase variation to be equal to or greater than 0° and smaller than 90°, the user such as a doctor becomes able to observe the vocal cords that undergo natural changes according to the desired change rate.

Moreover, according to the first embodiment, when the determining unit 53 determines that the variation in the vibrational frequency of the vocal cords of the subject is equal to or greater than a threshold value, the setting unit 55 varies the selection period that enables the selecting unit 56 to perform selection. Hence, from among a plurality of images, the most suitable images can be selected by conforming with the fluctuation in the vibrational frequency of the vocal cords of the subject.

Furthermore, according to the first embodiment, when the phase variation is equal to 0, if an instruction signal is input from the input unit 54 as an instruction to vary the initial phase of the selection period, the setting unit 55 varies the initial phase of the selection period according to the instruction signal input from the input unit 54. Hence, the user such as a doctor becomes able to observe the vocal cords of the subject in the desired condition and in the virtually-stopped state.

Moreover, according to the first embodiment, in the recording unit 58, the images selected by the selecting unit 56 from among a plurality of images input from the endoscope 2 are recorded along with added information indicating that the images have been displayed in the display device 4. Hence, after ending the observation of the vocal cords of the subject, if the same images are to be checked again, they can be checked with ease. In addition, also regarding a subject (patient) for whom the observation cannot be done in the quasi-slow-motion observation mode, since a plurality of images is recorded, the vocal cords can still be observed.

Second Embodiment

Given below is the explanation of a second embodiment. In the second embodiment, the configuration is different than the imaging system 1 according to the first embodiment described above, and the quasi-slow-motion observation mode processing is also different. More particularly, in the first embodiment, the determining unit 53 determines whether or not the vibrational frequency of the vocal cords of the subject, who represents a photographic subject, as detected by the detecting unit 51 is equal to or greater than a threshold value. In the second embodiment, the determination about whether or not the vibrational frequency of the vocal cords of the subject is equal to or greater than a threshold value is performed in each cycle. In the following explanation, the configuration of an imaging system according to the second embodiment is explained, and that is followed by the explanation of the quasi-slow-motion observation mode processing performed in that imaging system. Herein, the configuration identical to the configuration of the imaging system 1 according to the first embodiment is referred to by the same reference numerals, and the detailed explanation is not given.

Configuration of Imaging System

Figure 17:
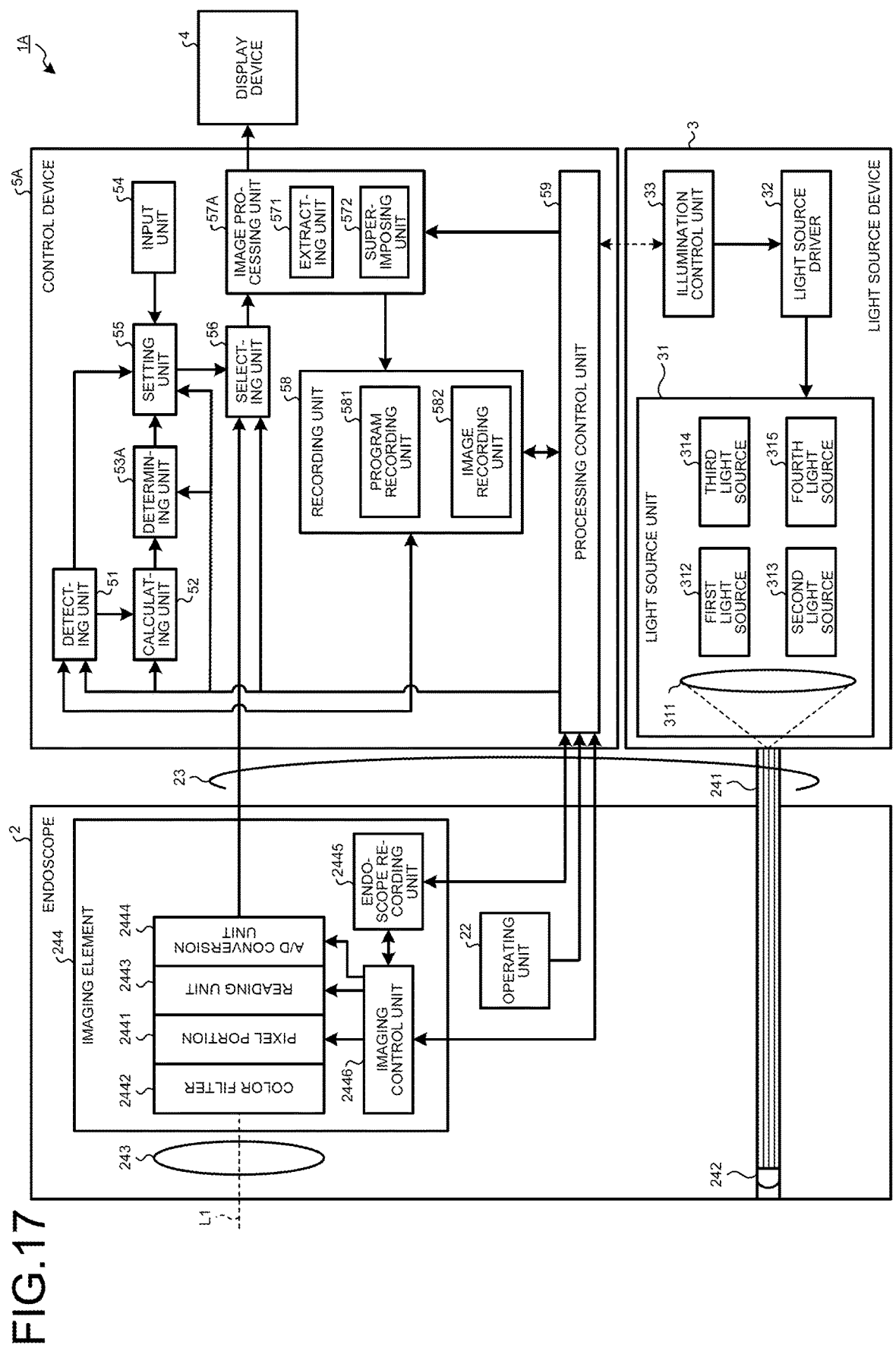
FIG. 17 is a block diagram illustrating a functional configuration of an imaging system according to a second embodiment.

FIG. 17 is a block diagram illustrating a functional configuration of the imaging system according to the second embodiment. An imaging system 1A illustrated in FIG. 15 includes a control device 5A in place of the control device 5 according to the first embodiment. The control device 5A includes a determining unit 53A and an image processing unit 57A in place of the determining unit 53 and the image processing unit 57, respectively, according to the first embodiment. In the second embodiment, the control device 5A functions as an image processing device.

The determining unit 53A determines whether or not, in each cycle of fluctuation of the vocal cords of the subject captured in the image displayed as the display image in the display device 4, the variation calculated by the calculating unit 52 is equal to or greater than a threshold value.

The image processing unit 57A has the same functions as the functions of the image processing unit 57 according to the first embodiment, as well as includes an extracting unit 571 and a superimposing unit 572.

The extracting unit 571 extracts abnormal regions captured in each of a plurality of images generated by the imaging element 244 of the endoscope 2. More particularly, the extracting unit 571 extracts, from each of a plurality of images, regions having the feature quantity equal to or greater than a predetermined threshold value as the abnormal regions. The feature quantity implies, for example, the red component or the yellow component. Meanwhile, the extracting unit 571 can perform known template matching and extract abnormal regions from a plurality of images.

The superimposing unit 572 superimposes the abnormal regions, which are extracted by the extracting unit 571, onto the image selected by the selecting unit 56; and outputs the resultant image to the display device 4.

Overview of Quasi-Slow-Motion Observation Mode Processing

Figure 18:
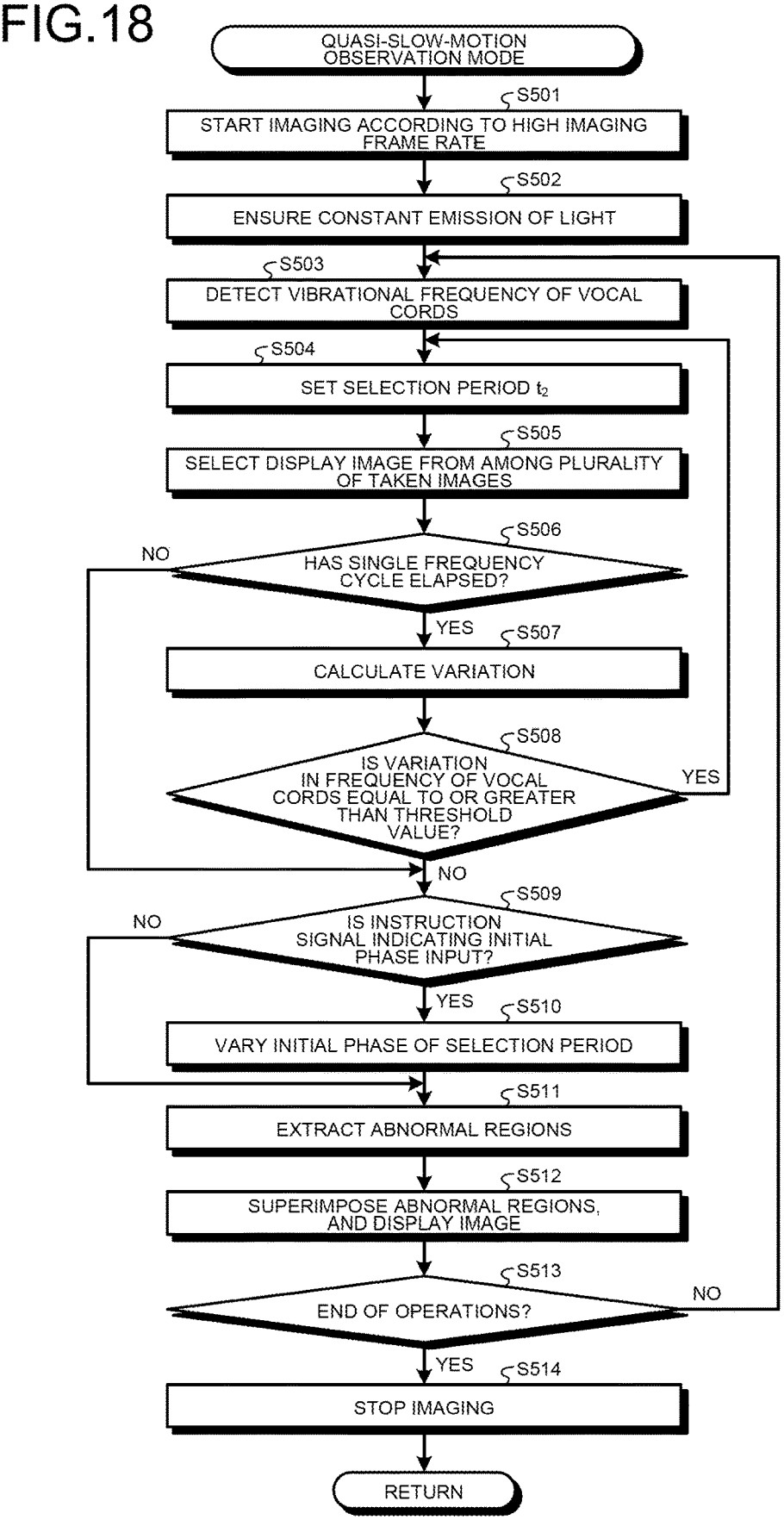
FIG. 18 is a flowchart for explaining the overview of quasi-slow-motion observation mode processing performed in the imaging system according to the second embodiment.

Given below is the explanation of the quasi-slow-motion observation mode processing performed in the imaging system 1A. FIG. 18 is a flowchart for explaining the overview of the quasi-slow-motion observation mode processing performed in the imaging system 1A. In FIG. 18, the operations performed from Step S501 to Step S505 correspond to the operations performed from Step S401 to Step S405 illustrated in FIG. 16.

At Step S506, the determining unit 53A determines whether or not a single cycle of the vibrational frequency of the vocal cords has elapsed. If the determining unit 53A determines that a single cycle of the vibrational frequency of the vocal cords has elapsed (Yes at Step S506), then the system control proceeds to Step S507 (explained later). On the other hand, if the determining unit 53A determines that a single cycle of the vibrational frequency of the vocal cords has not elapsed (No at Step S506), then the system control proceeds to Step S509 (explained later).

The operations performed from Step S508 to Step S510 correspond to the operations performed from Step S407 to Step S409 illustrated in FIG. 16.

At Step S511, the extracting unit 571 extracts abnormal regions from each of a plurality of images generated by the imaging element 244 of the endoscope 2.

Then, the superimposing unit 572 superimposes the abnormal regions, which are extracted by the extracting unit 571, onto the image selected by the selecting unit 56, and outputs the resultant image to the display device 4 (Step S512). After the operation at Step S512 is performed, the system control proceeds to Step S513. The operations performed at Steps S513 and S514 correspond to the operations performed at Steps S410 and S411 illustrated in FIG. 16.

According to the second embodiment, in an identical manner to the first embodiment, a simple configuration with a high degree of general versatility can be achieved; and the vocal cords of the subject, who represents a photographic subject, can be observed in real time.

Moreover, according to the second embodiment, the superimposing unit 572 superimposes the abnormal regions, which are extracted by the extracting unit 571, onto the image selected by the selecting unit 56, and outputs the resultant image to the display device 4. That enables the user such as a doctor to intuitively understand the abnormal regions.

Furthermore, according to the second embodiment, the determining unit 53A determines whether or not, in each cycle of fluctuation of the vocal cords of the subject captured in the image displayed as the display image in the display device 4, the variation is equal to or greater than a threshold value. Hence, even if the vibrational frequency undergoes changes during the observation, it becomes possible to observe the fluctuation in the vocal cords at a series of frequencies of the vocal cords.

Other Embodiments

The constituent elements of the imaging system according to the first and second embodiments can be appropriately combined and various other embodiments can be formed. For example, some or all of the constituent elements of the imaging system according to the first and second embodiments of the disclosure can be deleted. Moreover, the constituent elements of the imaging system according to the embodiment of the disclosure can be appropriately combined.

In the imaging system according to the first and second embodiments, the control device includes a detecting unit that detects the vibrational frequency of the vocal cords of the subject, who represents a photographic subject, based on a plurality of images. Alternatively, a plurality of images can be sent, via a network, to a learning model that is meant for detecting the vibrational frequency of the subject, and then the vibrational frequency of the subject can be received from the learning model.

Moreover, in the first and second embodiments, the explanation is given about a flexible endoscope. However, that is not the only possible case. Alternatively, the first and second embodiments can be applied in a rigid endoscope too.

Furthermore, in the imaging system according to the first and second embodiments of the disclosure, the term "unit" mentioned above can be read as "device" or "circuit". For example, a control unit can be read as a control device or a control circuit.

A computer program executed in the imaging system according to the first and second embodiments of the disclosure is recorded as installable file data or executable file data in a compact disc read only memory (CD-ROM), a flexible disk (FD), a compact disc recordable (CD-R), a digital versatile disk (DVD), a USB medium (USB stands for Universal Serial Bus), or a flash memory.

Alternatively, the computer program executed in the imaging system according to the first and second embodiments of the disclosure can be stored in a downloadable manner in a computer connected to a network such as the Internet.

Meanwhile, in the explanation of the flowchart given in the present written description, the context is explicitly illustrated using expressions such as "firstly", "then", and "subsequently". However, the sequence of operations required to implement the disclosure are not uniquely fixed by those expressions. That is, the sequence of operations illustrated in the flowcharts given in the present written description can be varied without causing contradiction.

Herein, although the disclosure is described with reference to the abovementioned embodiments for a complete and clear disclosure, the appended claims are not to be thus limited but are to be construed as embodying all modifications and alternative constructions that may occur to one skilled in the art that fairly fall within the basic teaching herein set forth.

According to the disclosure, it becomes possible to observe, in real time, the actions of a photographic subject performing high-speed vibration, high-speed rotation, or high-speed movement.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An image processing device comprising:
a processor comprising hardware, the processor being configured to:
obtain images captured by an imaging element configured to perform imaging at a higher frequency than a vibrational frequency of a subject;
detect the vibrational frequency of the subject based on the obtained images;
set a selection period that is longer than a vibration period of the subject;
sequentially select, from among the obtained images, images to be displayed on a display based on the selection period;
output the selected images;
wherein the processor is further configured to set the selection period based on
the vibration period of the subject,
a imaging frame rate of the imaging element,
a display frame rate of the display, and
a phase variation of each display period that is preset for display purpose on the display,
wherein the processor is further configured to:
calculate a variation of vibrational frequency of the subject;
determine whether or not the variation is equal to or greater than a threshold value; and
when it is determined that the variation is equal to or greater than the threshold value, vary the selection period, and
wherein the processor is further configured to determine whether or not, in each cycle of fluctuation of the subject in the images displayed on the display, the variation is equal to or greater than the threshold value.

2. The image processing device according to claim 1, wherein the processor is further configured to set the phase variation to be equal to or greater than 0° and smaller than 90°.

3. The image processing device according to claim 1, wherein, in a case in which the phase variation is equal to 0, when an instruction signal is input as an instruction to vary an initial phase of the selection period, the processor is further configured to vary the initial phase of the selection period according to the instruction signal.

4. The image processing device according to claim 3, further comprising a memory configured to sequentially record the images in chronological order.

5. The image processing device according to claim 4, wherein the memory is configured to record an image selected from among the obtained images, along with information indicating that the image has been displayed on the display.

6. The image processing device according to claim 5, wherein the processor is further configured to:
extract an abnormal region from each of the images; and
superimpose the extracted abnormal region onto the selected images; and
output the superimposed images to the display.

7. The image processing device according to claim 1, wherein the processor is further configured to use a learning model that
performs machine learning using, as teacher data, a plurality of images or videos of vocal cords of a plurality of subjects previously captured for each band frequency of the vocal cords of the plurality of subjects, and
outputs, as an output, a vibrational frequency of a vocal cord of a subject.

8. An imaging system comprising:
the image processing device according to claim 1; and
an imaging device, wherein
the imaging device includes an imaging element configured to perform imaging at a higher frequency than a vibrational frequency of the subject.

9. An image processing method implemented in an image processing device, the method comprising:
obtaining images captured by an imaging element configured to perform imaging at a higher frequency than a vibrational frequency of a subject;
detecting the vibrational frequency of the subject based on the obtained images;
setting a selection period that is longer than a vibration period of the subject;
sequentially selecting, from among the obtained images, images to be displayed on a display based on the selection period;
outputting the selected images;
setting the selection period based on
the vibration period of the subject,
a imaging frame rate of the imaging element,
a display frame rate of the display, and
a phase variation of each display period that is preset for display purpose on the display
calculating a variation of vibrational frequency of the subject;
determining whether or not the variation is equal to or greater than a threshold value; and
when it is determined that the variation is equal to or greater than the threshold value, vary the selection period, and
determining whether or not, in each cycle of fluctuation of the subject in the images displayed on the display, the variation is equal to or greater than the threshold value.

10. A non-transitory computer-readable recording medium with an executable program stored thereon, the program causing an image processing device to perform:
obtaining images captured by an imaging element configured to perform imaging at a higher frequency than a vibrational frequency of a subject;
detecting the vibrational frequency of the subject based on the obtained images;
setting a selection period that is longer than a vibration period of the subject;
sequentially selecting, from among the obtained images, images to be displayed on a display based on the selection period;
outputting the selected images;
setting the selection period based on
the vibration period of the subject,
a imaging frame rate of the imaging element,
a display frame rate of the display, and
a phase variation of each display period that is preset for display purpose on the display
calculating a variation of vibrational frequency of the subject;

determining whether or not the variation is equal to or greater than a threshold value; and when it is determined that the variation is equal to or greater than the threshold value, vary the selection period, and determining whether or not, in each cycle of fluctuation of the subject in the images displayed on the display, the variation is equal to or greater than the threshold value.

\* \* \* \* \*